(12) United States Patent
Potyrailo et al.

(10) Patent No.: US 7,691,329 B2
(45) Date of Patent: Apr. 6, 2010

(54) METHODS FOR DETECTING CONTAMINANTS IN A LIQUID

(75) Inventors: Radislav Alexandrovich Potyrailo, Niskayuna, NY (US); David James Monk, Rexford, NY (US); Ryo Tamaki, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 356 days.

(21) Appl. No.: 11/560,485

(22) Filed: Nov. 16, 2006

(65) Prior Publication Data

US 2008/0116908 A1    May 22, 2008

(51) Int. Cl.
*G01N 27/00* (2006.01)

(52) U.S. Cl. .................. 422/82.01; 73/53.01; 422/68.1; 422/81; 422/82; 422/82.02; 324/71.1; 324/691; 324/720

(58) Field of Classification Search ................. 422/68.1, 422/82–82.03
See application file for complete search history.

(56) References Cited

U.S. PATENT DOCUMENTS

| | | | |
|---|---|---|---|
| 3,607,084 A * | 9/1971 | Mackey et al. ............... | 436/152 |
| 3,999,122 A * | 12/1976 | Winstel et al. ............. | 324/71.1 |
| 4,822,744 A * | 4/1989 | Bellows ....................... | 436/38 |
| 4,941,958 A | 7/1990 | Byers | |
| 5,344,546 A * | 9/1994 | Kiesele et al. ............... | 204/415 |
| 5,344,547 A | 9/1994 | Vlasov et al. | |
| 5,591,321 A * | 1/1997 | Pyke ........................... | 205/787 |
| 5,840,168 A | 11/1998 | Chaniotakis et al. | |
| 5,879,630 A * | 3/1999 | Lescouzeres et al. ...... | 422/82.02 |
| 6,025,725 A | 2/2000 | Gershenfeld et al. | |
| 6,359,444 B1 | 3/2002 | Grimes | |
| 6,398,931 B1 | 6/2002 | Burshette et al. | |
| 6,586,946 B2 | 7/2003 | Hefti et al. | |
| 6,618,603 B2 * | 9/2003 | Varalli et al. ................. | 600/345 |
| 6,730,201 B1 | 5/2004 | Kuhlman et al. | |
| 6,780,307 B2 | 8/2004 | Kidwell | |
| 6,953,520 B2 | 10/2005 | Yengoyan et al. | |

(Continued)

FOREIGN PATENT DOCUMENTS

WO            0223176            3/2002

OTHER PUBLICATIONS

O'Brien et al., SPR biosensors: simlutaneously removing thermal and bulk-composition effects, 1999, Elsevier Science, Biosensors & Bioelectronics, 14, p. 145-154.*

(Continued)

*Primary Examiner*—Tony G Soohoo
*Assistant Examiner*—Robert Eom
(74) *Attorney, Agent, or Firm*—Ann M. Agosti

(57) ABSTRACT

In one embodiment, a method for detecting contaminants in a liquid comprises: contacting a sensor with a liquid, generating electrical information based upon a concentration of the contaminant in the liquid, transmitting the electrical information to a controller, and determining the concentration of a contaminant in the liquid. The sensor can comprise a film, a purge chamber, and a transducer, which are configured such that a first surface of the film is in fluid communication with the liquid and the purge chamber is in fluid communication with a second surface of the film that is opposite the first surface, and wherein the transducer is in fluid communication with the purge chamber.

18 Claims, 16 Drawing Sheets

U.S. PATENT DOCUMENTS

| | | |
|---|---|---|
| 2006/0020427 A1 | 1/2006 | Kahn et al. |
| 2006/0065530 A1 | 3/2006 | Yengoyan et al. |
| 2006/0081471 A1 | 4/2006 | Kidwell |

OTHER PUBLICATIONS

Ceresa, A., et al.; "Rational Design of Potentiometric Trace Level Ion Sensors. A Ag+-Selective Electrode with a 100 ppt Detection Limit"; Anal. Chem.; 2002;74; 4027-4036, Aug. 15, 2002.

Chinowski, T. M., et al.; "Experimental data from a trace Metal sensor combining surface plasmon resonance with anodic Stripping voltametry"; Sens. Actuators; B; 1997; 33-36 &37-43.

Chyan, O., et al.; "Ultrapure water quality monitoring by a silicon-based potentiometric sensor"; Analyst; 2000;125; 175-178, Nov. 9, 1999.

De Borba, B.M., et al.; "Determination of sodium at low Ng/1 concentrations in simulated power plant waters by ion Chromatography"; J. Chromatogr. A; 2003; 995; 143-152, Mar. 11, 2003.

Di Natale, C., et al.; "Multicomponent analysis of heavy Metal cations and inorganic anions in liquids by a non-selective Chalcogenide glass sensor array"; Sens. Actuators; B; 1996; 34; 539-542, May 3, 1996.

Di Natale, C., et al.; "Multicomponent analysis on polluted Waters by means of an electronic tongue"; Sens. Actuators; B;1997; 44; 423-428, May 14, 1997.

Ervin, A. M., et al.; "Development of a fiber-optic sensor for trace metal detection in aqueous environments"; Appl. Opt.;1993; 32; 4287-4290, Aug. 1, 1993.

Johns, C., et al.; "Sensitive indirect photometric detection of inorganic and small organic anions by capillary Electrophoresis using Orange G as a probe ion"; Electrophoresis;2003; 24; 557-566.

Jurs, P.C., et al.; "Computational Methods for the Analysis of Chemical Sensor Array Data from Volatile Analytes"; Chem. Rev.; 2000; 100; 2649-2678, Aug. 5, 1999.

Legin, A. V., et al.; "Development and analytical evaluation of a multisensor system for water quality monitoring"; Sens. Actuators; B; 1995; 27; 377-379.

Legin, A. V., et al.; "The features of the electronic tongue in Comparison with the characteristics of the discrete ion-selective Sensors"; Sens. Actuators; B; 1999; 58; 464-468, Jan. 19, 1999.

Mourzina, Y. G., et al.; "Development of multisensor Systems based on chalcogenide thin film chemical sensors for the simultaneous multicomponent analysis of metal ions in complex solutions"; Electrochimica Acta; 2001; 47; 251-258, Mar. 29, 2001.

Mullen, K. I., et al., "Trace detection of ionic species with Surface enhanced Raman spectroscopy"; Spectroscopy; 1992;7; 24-32, Jun. 1992.

Vlasov, Y. G., et al.; "Electronic tongue—new analytical Tool for liquid analysis on the basis of non-specific sensors and methods of pattern recognition"; Sens. Actuators;B; 2000;65; 235-256, Jun. 15, 1999.

Vlasov, Y., et al.; "Cross-sensitivity evaluation of chemical Sensors for electronic tongue: determination of heavy metallons"; Sens. Actuators; B; 1997; 44; 532-537, Jun. 11, 1997.

SE 07464SE/BR/BR Search Report, Oct. 8, 2008.

E. Malinowska et al., "Enhanced Electrochemical Performance of Solid-State Ion Sensors Based on Silicone Rubber Membranes," The 8th International Conference on Solid-State Sensors and Actuators, and Eurosensors IX, Stockholm, Sweden, Jun. 25-29, 1995. pp. 851-854.

* cited by examiner

Scores Plot

Original

Automatic drift correction

METHODS FOR DETECTING CONTAMINANTS IN A LIQUID

BACKGROUND

Disclosed herein are apparatus and methods for detecting and quantifying contaminants in a liquid, and systems for use thereof.

The detection of trace (e.g., less than 1% by volume) and microtrace (e.g., less than $1.0 \times 10^{-6}$% by volume) levels of chemical contaminants in aqueous solutions is important for monitoring the condition of numerous applications. For example, ultrapure water (i.e. water having a microtrace concentration of ionic species) is desirable in many industrial processes including, but not limited to, the semiconductor, pharmaceutical, agricultural, chemical, energy, and food processing industries. In one specific example, nuclear reactors can employ ultrapure water for cooling purposes. The ultrapure water can comprise contaminants, which cause corrosion and other problems in the reactors fluid handling system. Therefore, a system and method for detecting and quantifying these contaminants is extremely desirable.

The detection of chemical contaminants has evolved significantly over the last few decades. There are several techniques currently available for the detection and quantification of trace levels of ionic species in aqueous solutions. These techniques include ion chromatography (IC), inductively coupled plasma atomic emission spectrometry (ICP), mass spectrometry (MS), ICP-MS, and capillary electrophoresis (CE). Additionally, electrochemical, optical, and hybrid chemical sensors (e.g., combinations of different techniques such as surface plasmon resonance with anodic stripping voltammetry), have been applied for trace analysis of ionic species in water. Unfortunately, these methods can require extensive sample preparation or are limited by poor selectivity, inadequate detection limits, interference effects, baseline drift, and contamination during sampling or handling.

IC is the primary means of ionic species detection in aqueous solutions. For example, nuclear power plants have predominantly used in-line ion chromatography for routine monitoring of ionic species. IC methods originally comprised column ion exchange chromatography, which required large sample volumes, wet chemical analysis of collected fractions, and took hours to perform. More recently, IC methods have been developed that require significantly smaller sample volumes, operate virtually unattended under computer control, and can be conducted in only minutes. However, modern IC methods still suffer from disadvantages that make their use impractical in many situations, such as expense, complexity, and maintenance. Furthermore, the IC's currently attain an analysis time of approximately ten minutes, which is still too long in many applications.

ICP and ICP-MS are also used for ionic species detection. Inductively coupled plasma-isotope dilution mass spectrometry (ICP-IDMS) is suitable as a routine method for trace element and element speciation analysis; however, it is limited by the lack of commercially available isotope-labeled spike compounds for species-specific isotope dilution and by the complicated system set-up required for species-unspecific ICP-IDMS analysis. Therefore, there is a strong need to develop a more suitable detection method.

CE, which employs 10 to 100 times lower effluent volumes and provides a quicker measurement time than IC (typically less than a three minutes), is another common means of detecting ionic species. CE also has its limitations, e.g., there are practical limits to the amount of voltage that can be applied and to the shortness of the capillary tube. Further, the sample must be introduced in a band of finite width, and a finite volume is needed for reliable detection. Additionally, the heating of the electrolyte in the tube due to extremely high voltage gradients causes problems, such as undesirable zone broadening or even boiling of the electrolyte and a total breakdown of the electrophoretic process. Such limitations make the use of capillary zone electrophoresis impractical for many applications.

In light of the drawbacks associated with the current techniques employed for the detection and quantification of species in aqueous solutions, there is a current need for a detection method and a detection system that is free from the aforementioned limitations as well as limitations such as significant interference effects, baseline drift, and unintended water contamination due to handling.

BRIEF DESCRIPTION

Disclosed herein are an apparatus and method for determining the concentration of contaminants within a liquid, and systems for use thereof.

In one embodiment, a method for detecting contaminants in a liquid comprises: contacting a sensor with a liquid, generating electrical information based upon a concentration of the contaminant in the liquid, transmitting the electrical information to a controller, and determining the concentration of a contaminant in the liquid. The sensor can comprise a film, a purge chamber, and a transducer, which are configured such that a first surface of the film is in fluid communication with the liquid and the purge chamber is in fluid communication with a second surface of the film that is opposite the first surface, and wherein the transducer is in fluid communication with the purge chamber.

In another embodiment, a method for detecting a contaminant in a liquid comprises: contacting a sensor with a liquid, generating electrical information based upon a concentration of the contaminant in the liquid and determining the electrical conductivity of the sample, transmitting the electrical information and electrical conductivity to a controller, determining the concentration of the contaminant, and correcting the concentration of the contaminant based upon the electrical conductivity.

In yet another embodiment, a method for operating an apparatus for the detection of contaminants within water of a nuclear reactor comprises: contacting a sensor array with a sample of the water, generating electrical information from a sensor in the sensor array; and determining the concentration of the contaminant based upon the electrical information. Each sensor in the array comprises a film disposed on a transducer, and the film allows diffusion of the specific ion.

The above described and other features are exemplified by the following figures and detailed description.

BRIEF DESCRIPTION OF THE DRAWINGS

Refer now to the figures, which are exemplary embodiments, and wherein the like elements are numbered alike.

DETAILED DESCRIPTION

Disclosed herein is an apparatus and method for the detection and quantification of contaminants in a liquid (e.g., in an aqueous solution). The apparatus for detection, referred to as the contaminant detection system (hereinafter referred to as CDS), comprises a controller connected in operational communication to a sensor that is disposed in an aqueous solution. The sensor comprises transducer(s) and chemically responsive film(s) (hereinafter referred to as FILM) that are integrated with a manifold. The method for detection comprises analyzing the aqueous solution for contaminants, detecting a measured signal, and determining the concentration of an impurity in the solution.

Figure 1:
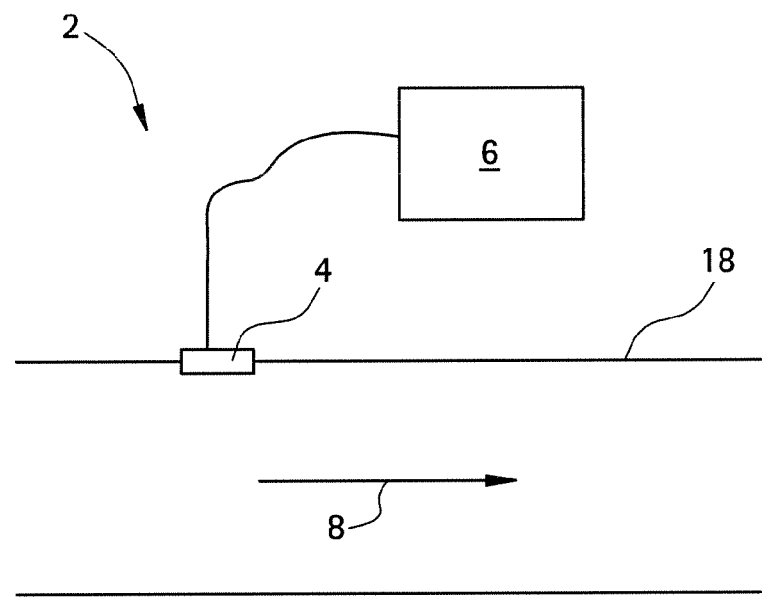
FIG. 1 is an illustration of an exemplary contaminant detection system (CDS).

Referring now to FIG. 1, an exemplary contaminant detection system (CDS) 2 is illustrated, wherein a controller 6 is operably connected to a sensor 4. The sensor 4 is disposed in fluid communication with a liquid 8, which can be flowing through a conduit 18. The sensor 4 is capable of providing information to the controller 6 which can be utilized to determine the concentration of contaminants (e.g., ionic species) within the liquid 8.

Figure 2:
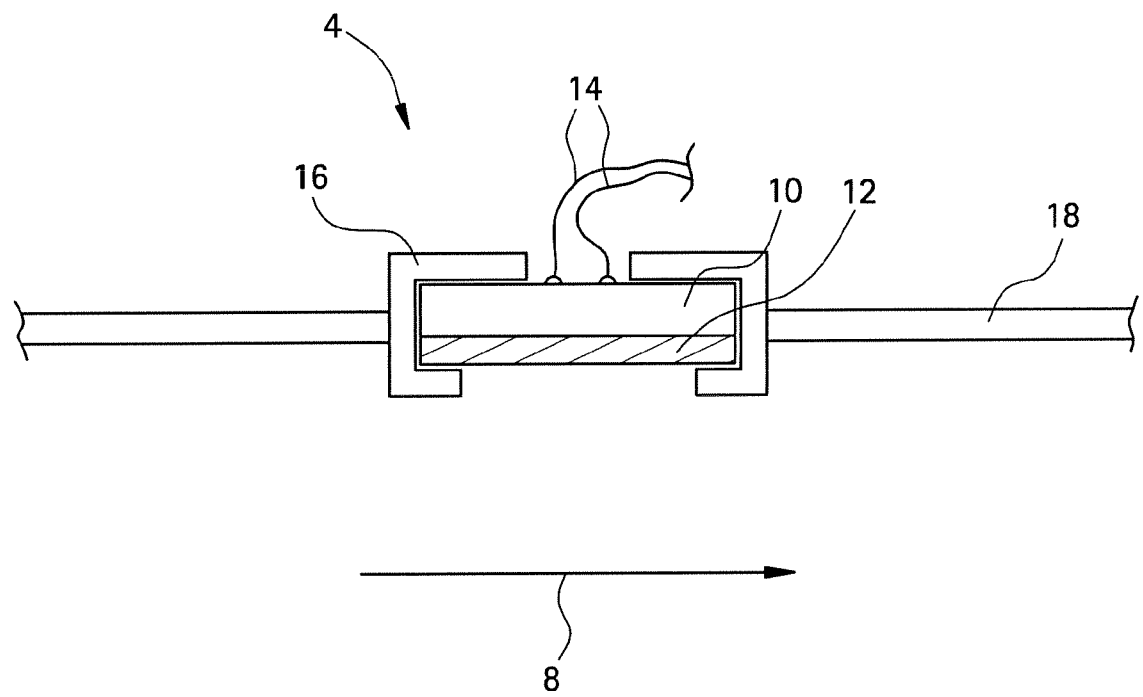
FIG. 2 is a cross-sectional view of an exemplary sensor.

Referring now to FIG. 2, an exemplary sensor 4 is illustrated which comprises a transducer 10 that is disposed in contact with a film 12, wherein both are disposed within a manifold 16. A surface of the film 12 that is opposite the surface in contact with the transducer 10 is disposed in fluid communication with the liquid 8, which comprises trace levels (e.g., small quantities) of contaminants (not shown). Wires 14 are connected in electrical communication to the transducer 10 and to controller 6 (not shown) to provide electrical communication therebetween. Although the current embodiment employs wires 14, it is to be apparent that alternative embodiments can achieve communications between the transducer 10 and the controller 6 without the use of wires 14, such as using wireless communications (e.g., radio-frequency communications using a RFID transducer). Further, the communications for any of the embodiments described herein can utilize any novel or known communication standard (e.g., Bluetooth (industrial specification for wireless personal area networks (PANs), also known as IEEE 802.15.1.), DECT (digital European cordless telephone), DSRC (dedicated short range communications), HIPERLAN (high performance radio local area network (set of local area network communication standards)), HIPERMAN (high performance radio metropolitan area network), IEEE (Institute for Electrical Engineers), IRDA (Infrared Data Association standards), RFID (radio frequency identification), WiFi (wireless fidelity), WiMAX (name commonly given to IEEE standard 802.16), xMAX (a radio frequency (RF) modulation and encoding technology), ZigBee (wireless network conforming to IEEE standard 802.15.4), and so forth, as well as combinations comprising at least one of the foregoing) to communicate between the transducer 10 and the controller 6.

During use, the sensor 4 is capable of providing information to the controller 6 that can be utilized to determine the concentration of a contaminant within the liquid 8. In general this is accomplished by employing the transducer 10 to provide electrical information to the controller 6, which varies based on the quantity of ions that pass through the film 12. To enable the controller to determine the concentration of a specific contaminant within the liquid 8, the film 12 is configured to allow the passage of a desired contaminant (e.g., the ions of the contaminant that are being evaluated) and restrict, either partially or completely, the passage of non-desired contaminants (e.g., additional contaminant that are not being evaluated) through the film 12.

The film 12 generally comprises a polymeric material that is chosen based on its ability to allow the passage of the specific contaminant therethrough. To be more specific, an exemplary polymeric material employed for the film 12 can have a glass transition temperature that is below the temperature at which the sensor will operate, thereby providing a semi-viscous state, which enables the diffusion of the specific contaminants therethrough. Additives can be incorporated within the polymeric materials employed for the film 12 to tailor the diffusion of species in the film 12. Once a film 12 exhibits a desirable glass transition temperature and/or rate of diffusion, the polymer matrix can then be doped with an ion exchange material having a positive or negative charge. The specific ion exchange material will be based on the charge of the contaminants within the liquid that are to be analyzed. For example, ion exchange materials having a negative charge are used for positively charged contaminants, positively charged ion exchange materials are used for negatively charged contaminants. It is also to be understood that neutral charged films can be used for contaminants having a neutral charge. For detection of ions in water, the film composition is chosen to provide a selective binding process of an ion of interest using ionophores. Ionophores are added to the polymeric material to increase the selectivity of the film 12 and to further facilitate the transport of the contaminant through the film.

Likewise, ionophores and/or ion exchange materials can also be added to the polymeric material to limit the diffusion of non-desired contaminants (e.g., interferants) through the film 12. Examples of ionophores for sulfate detection are zinc phthalocyanine and 1,3-[bis(3-phenylthioure-idomethyl)] benzene. Examples of ionophores for chloride detection include 4,5-bis-[N'-(butyl)thioureido]-2,7-di-tert-butyl-9,9-dimethylxanthene and meso-tetraphenylporphyrin manganese(III). Examples of ionophores for zinc detection include 3-[(2-furylmethylene)amino]-2-thioxo-1,3-thiazolidin-4-one and 1-(2-pyridylazo)-2-naphthol. Plasticizers can be added to a polymer sensor film formulations as a lipophilic phase to facilitate ion transport in the sensor film (for example, bis(2-ethylhexyl) sebacate (DOS), 2-nitrophenyl octyl ether (NPOE), acetophenone (AP), dibutyl phthalate (DBP), nitrobenzene (NB). Other components can be also added to the sensor film composition, for example, ion exchangers (e.g. tridodecylmethylammonium chloride).

Polymer films can be used as the matrix material for ion sensors because they can exhibit inherent permselectivity that results from their chemical composition, they are available in a wide variety of chemistries, they are stable over long periods of time, and their physical and chemical properties and selectivity can be modified by the addition of other components (plasticizers, ion exchangers, ionophores, etc.). Permselectivity, a desirable trait, occurs because ions exhibit, to varying degrees, hydrophilic or lipophilic characteristics based on their hydration enthalpy.

Exemplary polymers that can be employed for the film 12 are polysulfone, polyaniline, poly(hydroxyethylmethacrylate), poly vinyl chloride, polyurethane, acrylate copolymer, and combinations comprising at least one of the foregoing polymers. In addition, polymers produced from the sol-gel reaction of silicon alkoxides (e.g., tetraethoxysilane (TMOS) or tetraethoxysilane (TEOS)) provides effective means to prepare silica through the hydrolysis and condensation reactions at ambient temperatures. The choice in the processing conditions such as the water to alkoxysilane ratio, pH, temperature, and the specific solvent employed, allows the control of the physical properties (e.g., pore size, surface area, and porosity) of the film 12. Organosilane precursors having the general formula $(R_{(4-x)}Si(OR')_x$, (wherein R and R' represents the desired reagent and/or functional group and X=1 to 3) can be hydrolyzed and condensed with or without the silicon alkoxides (i.e., TMOS or TEOS) to produce silica containing the target functional groups R covalently attached, which will effect the specific physical properties (e.g., mechanical flexibility, pore size, porosity and hydrophobicity) of the resulting material.

The mild condition of the sol-gel reaction allows the encapsulation of ion sensing reagents into the sol-gel matrix. These agents can be also covalently attached to the matrix by binding to the alkoxysilane precursors. Once these reagents are integrated into the matrix either by physical encapsulation or by chemical bonding, they form complex with the target contaminant upon exposure and provide signals through transducers. The porous nature of the sol-gel materials provides the sensing reagents high degree of freedom to move or to reorient inside the pores to form the complex. The flexibility can be further provided by replacing R of organosilane precursor with bulky groups such as phenyl, ethyl or benzyl groups or by reducing the number of alkoxy groups for example to two. The reduced cross-linking density with organo functional groups also contribute to the increase in the mobility of contaminants in the matrix and the reduction in the response time Some of the organo functional groups on the precursor silane increases the hydrophobicity of the silica network and prevents swelling in aqueous environments, which is beneficial for the discrimination of non-target contaminants.

In one specific embodiment, benzyltriethoxysilane can be used in combination with tetraethoxysilane to reduce the cross-linking density and to increase the hydrophobicity. In another embodiment, tetraethoxysilane, dimethyldiethoxysilane, methyltriehoxysilane, benzyltriethoxysilane, and combinations comprising at least one of the following can be employed as a precursor.

Exemplary materials that can also be employed for the film 12 comprise, polysulfones, poly(hydroxyethylmethacrylate), polyaniline, polyalkylenes (e.g., polyethylene, polypropylene, polyalkylene terephthalate (such as polyethylene terephthalate, polybutylene terephthalate)), polycarbonate, acrylic, styrenes (e.g., impact-modified polystyrene, acrylonitrile-butadiene-styrene, styrene-acrylonitrile), poly(meth)acrylate (e.g., polybutyl acrylate, polymethyl methacrylate), polyamines, polyamides, polyethers (e.g., polyetheresters and polyetherimides), polyesters, polyphenylene oxide, polyphenylene ether, polysiloxanes, polysaccharides, polysulfates, polysulfides, polyurethanes, polyvinyl acetates, polyvinyl alcohols, polyvinylchloride, and so forth, as well as combinations comprising at least one of the foregoing.

The thickness of the film 12 will affect the ionic transport therethrough. Therefore, the specific dimensions of the film will be determined based upon the desired ionic transport properties such as time, diffusion rate, and so forth. In one example, films 12 can be employed that comprise a thickness of about 0.1 to about 200 micrometers. In one specific example, a polysulfone film 12 can be employed that comprises a thickness of about 10 micrometers. In another specific example, a sol-gel film 12 can be employed having a thickness of about 100 micrometers.

Figure 3:
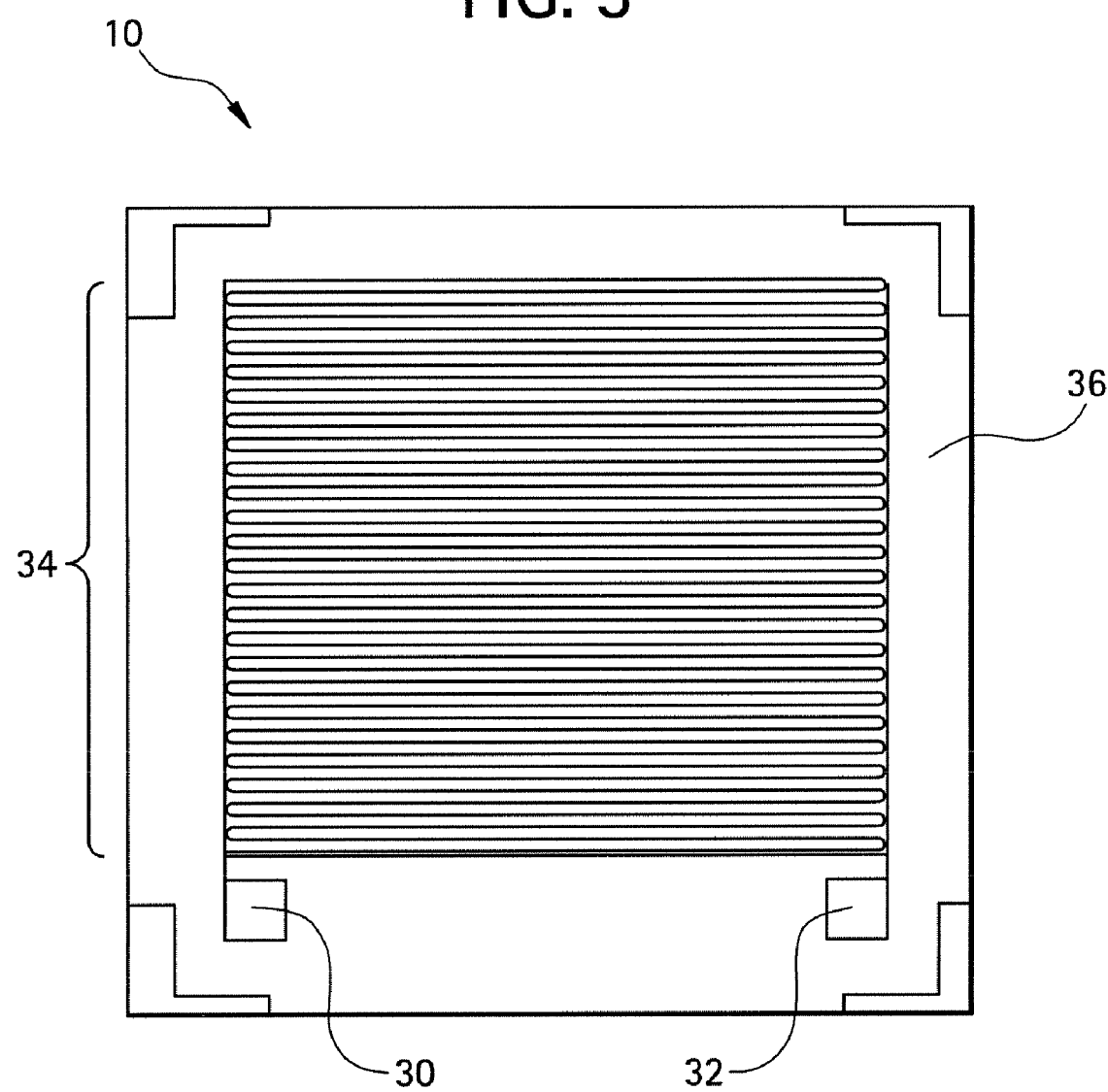
FIG. 3 is an illustration of an exemplary transducer.

The transducer 10 can be any electrochemical transducer that can provide information to the controller 6 which can be utilized to determine the concentration of a contaminant within the liquid 8. One exemplary transducer 10 is illustrated in FIG. 3, wherein an exemplary transducer 10 comprises a first electrode 30 and a second electrode 32 that are individually connected in electrical communication to interdigitated fingers 34 (combined these can generally be referred to as the electrode). The electrode is disposed on a base 36. The transducer 10 illustrated in FIG. 3 can be employed in any of the embodiments described herein and is not limited. It is to be understood that although several embodiments illustrate transducers 10 having wires 14, a wireless transducer is interchangeable therewith.

The first electrode 30, second electrode 32 and the interdigitated fingers 34 comprise a conductive metal (e.g., gold, platinum, or copper), metal alloys (e.g., nickel-copper alloys), or other conductive materials that enable the function of the transducer 10. The base 36 can comprise a polymeric film, such as polyimide or a material, such as silicon oxide, aluminum oxide, and so forth.

The exemplary transducer 10 illustrated within FIG. 3 operates based on the principle that the electrical properties measured by the controller 6 between the interdigitated fingers increases with the quantity of ions that pass through the film 12 and contact the transducer 10 (e.g., ions disposed in operational communication between the interdigitated fingers). The electrical properties measured can be complex impedance at multiple frequencies, electrochemically-modulated impedance, electrical current, and electrical potential, as well as combinations comprising at least one of the foregoing.

One exemplary method, the linear response method can be employed to measure impedance. To be more specific, in the linear response method, the system is perturbed by a sine wave current or potential having a small amplitude, which produces a response that contains only the first-order terms of the Taylor-expanded non-linear current-voltage relationship. Generally, two "modes" of operation of the method can be distinguished. The first mode is the measurement of the impedance as a function of the frequency of the small amplitude sinusoidal potential perturbation that is superimposed on a direct potential bias. The impedance spectrum is measured at varied values of the direct potential. This method is named Electrochemical Impedance Spectroscopy, or Impedance Voltammetry. The second mode is the superposition of a single-frequency sinusoidal potential on a scanned or stepped direct potential and measurement of the responding sinusoidal current as a function of the direct potential. This technique is named Alternating Current Polarography or Alternating Current Voltammetry. In this case essentially the reciprocal of the impedance, called admittance, is obtained.

Ion-selective conductometric microsensors do need a separate reference electrode, wherein the ion detection is accomplished by the measurement of the bulk conductance of a thin ion-selective film 12 that contains an ion-complexing agent. The magnitude of the signal (conductivity) can be related to the content of the primary ion in the analyzed water. To monitor the film 12 conductance it is deposited on top of a pair of thin-film interdigitated electrodes. The sensor operation is based on the specific and reversible ion co-extraction from the liquid into the sensing film that contains a specific ionophore. The ion co-extraction changes the bulk conductance. The ionophore in the film supports the specific solubilization of the cations into the film, which is simultaneously accompanied by the co-extraction of the anions in order to comply with the condition of electroneutrality. To minimize this anion interference, the liquid can be buffered with a large concentration of lipophilic anions.

In potentiometric sensors, the analytical information is obtained from the relationship between the potential of the working electrode coated with an ion-selective sensing film 12 and the contaminant concentration in the liquid. Because the potential of a single electrode cannot be measured, a reference electrode is used in combination with the working electrode. A sensing (or working) electrode of a potentiometric sensor is coated with a sensing film 12 also known as a sensing membrane. Such films 12 can be a formulated sol-gel, glass, or inorganic crystal or a formulated polymer film 12. The film 12 composition is chosen in order to impart a potential that is primarily associated with the ion of interest (e.g., the specific contaminant) via a selective binding process at the film-electrolyte interface. The magnitude of the surface potential of the film 12 is directly related to the activity or number of primary ions of interest in the liquid (e.g., the aqueous solution). The mechanisms and models that describe the selective response of potentiometric sensors to ions of interest include chemisorption and phase-boundary potential.

It is to be apparent that alternative transducers can be employed as well. For example a four-electrode transducer can be employed. Yet even further, a radio frequency identification (RFID) can be employed, wherein a RFID tag is coated with a sensing film to form an RFID sensor that can be employed as the transducer 10, or in combination with a transducer 10. In this embodiment, the RFID sensor can transmit information to a suitable device. Yet even further, the RFID sensor can be disposed within the conduit 18 and transmit information therethrough, wherein the conduit 18 comprises walls formed from nonconductive material(s), such as glass or plastic. These RFID sensors provide multi-parameter monitoring with an individual sensor with simultaneous digital ID functionality that automatically provides information about the sensor and its location (e.g., its correct assembly, production and expiration date, sensor calibrations, correction coefficients, and so forth). The radio frequency transducers can transmit the electrical information at a frequency of 80 kHz to 200 kHz; 5 MHz to 10 MHz; or 9 MHz to 16 MHz.

The liquid 8 can be delivered to the sensor 4 in bulk through a conduit 18 (e.g., a pipe, tube, and so forth), a vessel (e.g., container, test tube, flask, bottle, and so forth, not shown), or in a small quantity (e.g., such as supplied by a pipette). Regardless of the supply method or quantity, the liquid 8 can be preconditioned prior to contacting the sensor 4 such that the properties of the liquid 8 are modified and/or standardized. For example, the liquid 8 (e.g., an aqueous solution) can be temperature adjusted (e.g., heated or cooled), filtered, pressurized, stirred, mixed with chemical(s) (e.g., modifiers), and so forth, as well as combinations comprising at least one of the foregoing. Preconditioning the liquid 8 can be beneficial in systems wherein the sensor 4 (e.g., transducer 10 and/or film 12) is influenced by the characteristics of the liquid 8. In such systems, preconditioning can improve the repeatability and/or sensitivity of the sensor 4 or increase the sensors response, and so forth. For example, properties such ionic diffusion, conductivity, impedance, as well as other properties can be effected by the temperature of the liquid 8, which can influence the sensor 4 response. Further, the ability to precondition the liquid 8 offers the ability to analyze the liquid 8 under various conditions (e.g., temperature and/or pressure). For example, a test can be conducted wherein the liquid 8 is tested at multiple temperatures, which can provide additional information regarding the ionic transport of the contaminant of interest, or could even provide information regarding the presence of non-desired contaminants that could affect the electrical information supplied by the sensor 2, 40, and so forth.

The manifold 16 is employed to secure the transducer 10 and film 12. However, it is to be apparent that the manifold is not necessary in applications wherein the film 12 is bonded to the transducer 10. The manifold can comprise any material that is capable of securing the transducer 10 and the film 12, and is resistant to prolonged exposure (e.g., greater or equal to about six months, or more specifically greater than or equal to about one year) to the liquid 8.

Figure 4:
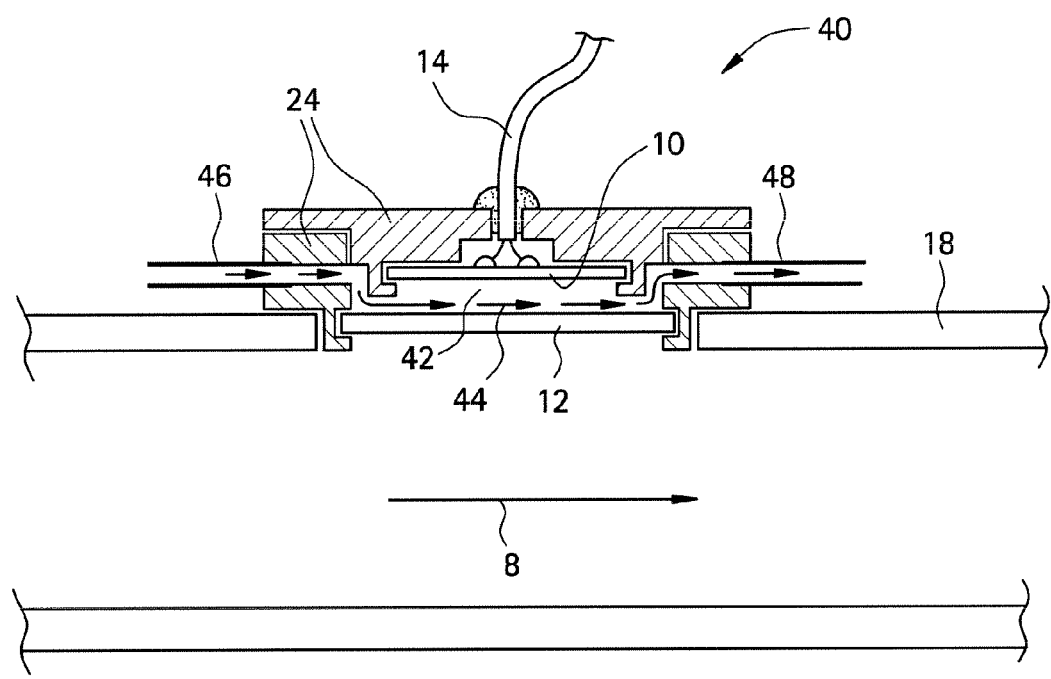
FIG. 4 is a cross-sectional view of an exemplary sensor.

Illustrated in FIG. 4, is a cross-sectional view of an exemplary sensor 40 comprising an alternative configuration, wherein a purge chamber 42 is disposed between a transducer 10 and a film 12. To be more specific, the sensor 40 comprises a film 12 disposed in fluid communication with a liquid 8 flowing within a conduit 18. A surface of the film 12 that is opposite the side in contact with the liquid is fluidly connected to a purge chamber 42, wherein a purge media 44 can flow. The purge chamber 42 is also defined by a transducer 10 that is disposed in fluid contact with the purge media 44 flowing within the purge chamber 42. On a side of the transducer 10 that is opposite the side in contact with the purge chamber 42, a wire 14 is connected in electrical communication to the transducer 10 and the controller 6 (not shown). The purge chamber 42 is further defined by the manifold 24, which secures the transducer 10, wire 14, and film 12. Also attached to the manifold 24 are an inlet 46 and an outlet 48, through which the purge media 44 can flow. Optionally, additional probes can be employed in the sensor. For example, conductivity probe(s) (not shown) can be located in contact with the liquid 8, e.g., in and/or outside of chamber 42. Similarly, temperature probe(s) (i.e., temperature sensors) can be located in thermal communication with the liquid to enable temperature determination. It is to be understood however, that a wireless transducer can be employed as an alternative or in addition to the transducer 10 illustrated.

In use, the sensor 40 is capable of providing information to the controller 6 that can be utilized to determine the concentration of a contaminant within the liquid 8. In general, the sensor 40 is operated in a sensing mode and a purge mode. In the sensing mode, flow of the purge media 44 is stopped, and ions from the liquid 8 migrate through the film 12 and diffuse into the purge media 44 within the purge chamber 42. The transducer 10 provides electrical information to the controller 6 (not shown) based on the quantity of ions that are diffused within the purge media 44. In a purge mode, the flow of the purge media 44 is initiated. Upon flowing of the purge media 44 through the purge chamber 42, a majority, or all, of the ions allowed to pass through the film 12 are purged (e.g., washed) from the purge chamber 42.

The ability to purge the sensor 40 of ions offers notable advantages. Firstly, the ability to purge enables the sensor to return to a calibrated state, or self-calibrate, between measurements. For example, if the sensor is calibrated in the presence of the purge media 44, after a purge mode, the sensor 40 will return to the calibrated condition. Further, if it is determined that benefits are exhibited by calibrating the sensor 40 prior to each sensing mode (e.g., improved measurement accuracy), the sensor 40 can be calibrated during the purge mode. A second notable advantage realized through the ability to purge the sensor 40 is the reduction of interference effects. To be more specific, the accuracy of the sensor 40 can be affected by the accumulation of non-desired contaminant (e.g., contaminants that are not be evaluated) within the sensor. This is due to the fact that the electrical information measured by the transducer 10 is effected by the accumulation of these non-desired contaminants. Therefore, the ability to purge these non-desired contaminants between measurements ensures their accumulation does not affect the sensors accuracy. Yet further, to purge the ions from the purge chamber, the purge media 44 can also be heated, pressurized, and/or diluted with a chemical reagent.

The purge media 44 employed will be capable of purging all, or a majority, of the ions that pass through the film 12 from the purge chamber 42. Further, the purge media 44 will be a purified form of the liquid 8. For example, in systems wherein water is the liquid 8, purified water is employed as the purge media 44.

The sensor 40 will provide an accurate measurement of the concentration of a contaminant within the liquid 8 when the concentration of the liquid 8 and the concentration of the contaminant within the purge chamber 42 equilibrate. Therefore, it is desirable to minimize the volume of the purge chamber. To do so, valves or other means of selectively hindering fluid communication between the purge chamber 42 and the inlet tube 46 and outlet tube 48 can be employed.

Figure 5:
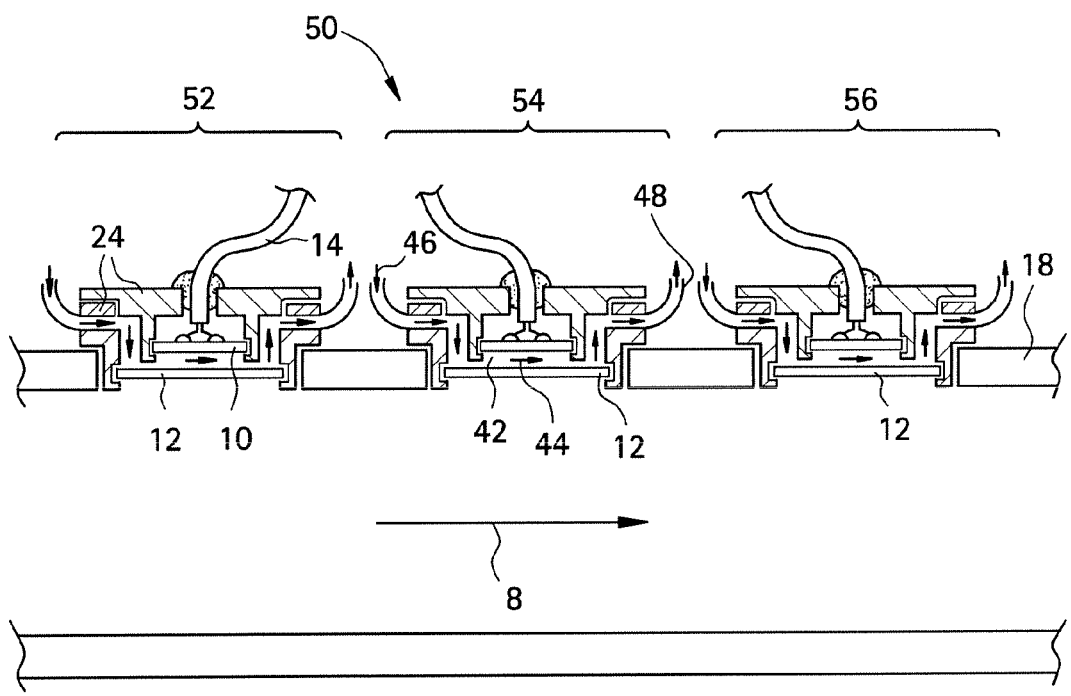
FIG. 5 is a cross-sectional view of an exemplary sensor array.

Referring now to FIG. 5, a cross-sectional view of an exemplary sensor array 50 is illustrated, wherein the sensor array 50 comprises a first sensor 52, a second sensor 54, and a third sensor 56 (collectively referred to as sensors), that are disposed in fluid communication with an liquid 8 flowing within a conduit 18. The sensor array 50 is capable of providing electrical information to a controller 6 from each of the sensors 40 via wires 14. Each sensor 40 is fluidly connected to an inlet tube 46 and an outlet tube 48 that are capable of supplying a purge media 44 to purge the purge chamber 42 within each sensor 40.

The sensor array 50 can be employed to determine an average contaminant concentration within the liquid 8. For example, the sensor array 50 can provide three sets of electrical information to the controller 6 (e.g., one set of electrical information for each sensor (52, 54, and 56). The information can then be analyzed, and an average contaminant concentration can be determined. In this embodiment, the sensors are configured similar to one another (e.g., having the same film 12).

In an alternative embodiment, the sensor array 50 can be capable of supplying electrical information to the controller 6 based upon the time dependent migration of the desired contaminant through the film 12. To be more specific, the duration of time required for the desired ion to pass through a film 12 is affected by presence and/or concentration of non-desired contaminant(s) within the liquid 8. Therefore, the sensors can comprise films 12 of the same material(s) (e.g., polysulfone) that differ in thicknesses. In this configuration, the duration of time required for the electrical information supplied by each sensor to reach a plateau, or reach a specific level, can be evaluated and utilized by the controller 6 to determine if non-desirable contaminants are affecting the ion transport of the desired contaminant and so forth.

In an alternative embodiment, the sensor array 50 can employ sensors 40 having differing films 12, which would therefore alter the electrical information supplied to the controller 6 by each sensor 40. For example, a sensor array 50 comprising differing sensors 40 can be employed to reduce interference caused by the presence of non-desirable contaminants within the liquid 8 for the purpose of increasing the accuracy of a measurement of the desired contaminant within the liquid 8. To be more specific, a first sensor can be employed to provide electrical information to the controller 6 based on a first contaminant, which is the desired contaminant to be measured. However, two addition contaminants, a second contaminant and a third contaminant, are known to obscure the accuracy of the first contaminant concentration within the liquid 8. Therefore, a sensor array 50 can be configured with a second sensor comprising a film 12 configured to allow the passage of the second contaminant therethrough, and a third sensor comprising a film 12 configured to allow the passage of the third contaminant therethrough. In this configuration, the electrical information supplied by the three sensors can be analyzed by the controller 6. If the controller 6 determines that the second sensor did not detect the second contaminant, and the third sensor did not detect the third contaminant, the information received from the first sensor (assuming the presence of the first contaminant) is determined to be accurate and not obscured by the presence of the second or third contaminant.

Further, in an alternative embodiment, if the presence of either the second contaminant or the third contaminant is determined, the controller 6 can be capable of accounting for the concentration of these contaminants to determine the accurate concentration of the first contaminant within the liquid 8.

Figure 6:
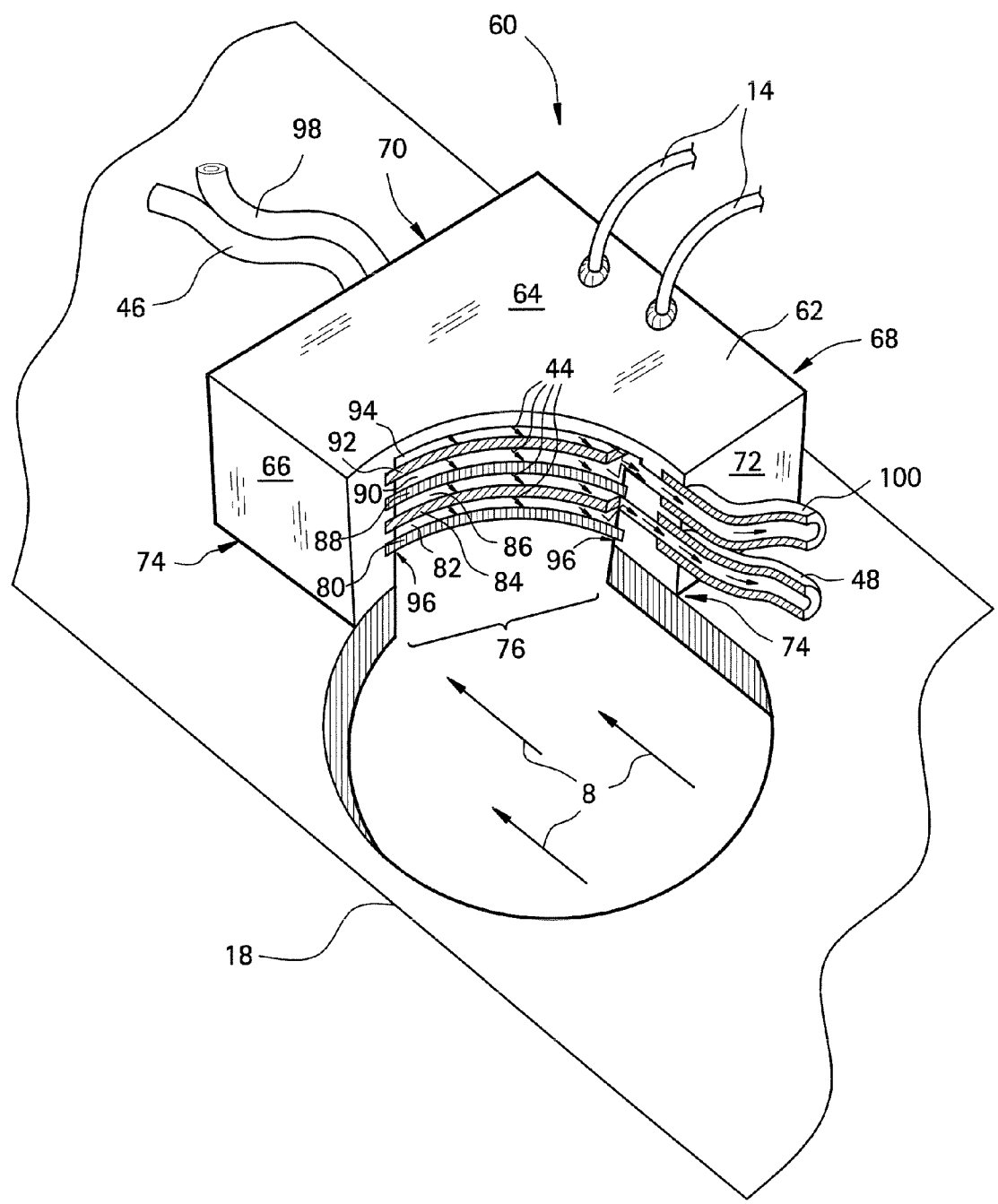
FIG. 6 a cross-sectional view of an exemplary sensor array.

Illustrated in FIG. 6, is a cross-sectional view of an exemplary sensor array 60, wherein the sensor comprises a stacked configuration. To be more specific, the sensor array 60 comprises a manifold 62 comprising a top surface 64, left side 66, a right side 68, a back side 70, a front side 72, and a bottom 74 (hereinafter if the terms top, left, right, back, front, or bottom are used they are used with respect to these designations). The bottom 74 of the manifold 62 is disposed in contact with a conduit 18 through which a liquid 8 flows. The manifold 62 comprises a test window 76 disposed through the bottom 74 of the manifold such that the liquid 8 is in fluid communication with a first film 80, which is secured on all edges 82 (e.g., back edge, left edge, right edge, and front edge) by the manifold 62 such that the liquid 8 cannot flow around the edges of the first film 80.

The first film 80 has a top surface that is opposite the bottom surface in contact with the liquid 8. The top surface is disposed in fluid communication with a first purge chamber 82, which is in fluid communication with the bottom surface of a first transducer 84. The top surface of the first transducer is 84 is in fluid communication with a second purge chamber 86, which is in fluid communication with a with the bottom surface of a second film 88. The top surface of the second film 88 is in fluid communication with a third purge chamber 90, which is in fluid communication with a with the bottom surface of a second transducer 92, The top surface of the second transducer is 92 is in fluid communication with a fourth purge chamber 94. Hereinafter, the first purge chamber 82, second purge chamber 86, third purge chamber 90, and fourth purge chamber 94 can be generally referred to as the purge chambers. Likewise, the first transducer 84 and the second transducer 92 can be referred to as the transducers, and, the first film 80 and second film 88 can be referred to as the films. The transducers 10 are connected in electrical communication to a controller 6 (not shown) by wires 14, or in an alternative embodiment, the transducers can be wireless.

The first transducer 84 and second transducer 92 are secured by the manifold 62 at the their left and right edges, and the front and back edges are not secured by the manifold 62. In this configuration, the first purge chamber 82 and the second purge chamber 86 are fluidly connected to each other and to an inlet tube 46 and an outlet tube 48. Likewise, the third purge chamber 90 and the fourth purge chamber 94 are fluidly connected to each other and to a second inlet tube 98 and a second outlet tube 100.

In operation, the sensor array 60 can be employed to determine an average contaminant concentration within the liquid 8. For example, the sensor array 60 can provide two sets of electrical information to the controller 6 (not shown). The information can then be analyzed, and an average contaminant concentration can be determined. To be more specific, the first film 80 can be configured to allow various contaminants within the liquid 8 to migrate therethrough and distribute themselves within the first purge chamber 82 and second purge chamber 86. Once therein, the contaminants affect the electrical information provided by the first transducer 84 to the controller 6. Likewise, the second film 88 can be configured to allow various contaminants within the first purge chamber 82 and second purge chamber 86 to migrate therethrough and distribute themselves within the third purge chamber 90. Once therein, the contaminants affect the electrical information provided by the second transducer 92 to the controller 6.

The second film 88 can comprise the same film material or a differing film material from the first film 80 to alter the specific contaminants that are allowed through each film (the first film 80 and the second film 88).

In one embodiment, the controller 6 can evaluate the electrical information supplied by the sensor array 60 based upon the time of the migration of the desired contaminant through the film 12. For example, if the first film 80 and the second film 88 comprised the same materials, the time elapsed before the electrical information supplied by the first transducer 84 is similar to the electrical information supplied by the second transducer 92 can be compared by the controller.

In another embodiment, the first film 80 and second film 88 can comprise the same film materials however differing thicknesses. In this configuration as well, the duration of time required for the electrical information supplied by each sensor to reach a plateau, or reach a specific level, can be evaluated and utilized by the controller 6 to determine if non-desirable contaminants are affecting the ion transport of the desired contaminant and so forth.

In an alternative embodiment, the first film 80 and the second film 88 can employ differing materials to reduce interference caused by the presence of non-desirable contaminants. To be more specific, the first film 80 can be configured to allow ion transport of the desired contaminant; however, a non-desired contaminant can migrate therethrough as well. The second film 88 can be configured to allow ion transport of a non-desired contaminant (but not allow the transport of the desired contaminant). In this configuration, the controller 6 can evaluate the electrical information supplied by the first transducer 84 and the second transducer 92 and determine if a non-desired contaminant is present and/or what concentration of the non-desired contaminant passed through the first film 80. The controller 6 can thereafter determine if the electrical information from the first transducer 84 accurately represents the concentration of the desired contaminant in the liquid 8. Further, if the presence of the second contaminant is determined, the controller 6 can be capable of accounting for its concentration and determining the accurate concentration of the desired contaminant (to be discussed further below).

In yet another embodiment, the first film 80 and the second film 88 can employ differing materials, and the first film 80 can be configured to allow ion transport of the desired contaminant; however, a non-desired contaminant can migrate through as well. However, the second film 88 can be configured to not allow ion transport of a non-desired contaminant and allow the transport of the desired contaminant. In this configuration, the controller 6 can evaluate the electrical information supplied by the first transducer 84 and the second transducer 92 and determine if a non-desired contaminant is present and/or what concentration of the non-desired contaminant passed through the first film 80. The controller 6 can thereafter determine if the electrical information from the first transducer 84 accurately represents the concentration of the desired contaminant in the liquid 8. Further, if the presence of the non-desired contaminant is determined, the controller 6 can be capable of accounting for its concentration and determining the accurate concentration of the desired contaminant (to be discussed further below).

The controller 6 can be any apparatus that is capable of receiving information from the sensors 4, 40 and/or sensor arrays 50, 60, interpreting the information, and determining the concentration of contaminants in the liquid 8. To be more specific, a computer (i.e., any electronic device capable of interpreting electronic information) can be employed that comprises a data acquisition system that is operably connected to the sensors (4, 40) and/or sensor arrays (50, 60). To be even more specific, a computer is a suitable electronic device capable of accepting data and instructions, executing the instructions to process the data, and presenting the results. Therefore, computer 64 can be a microprocessor, microcomputer, a minicomputer, an optical computer, a board computer, a complex instruction set computer, an ASIC (application specific integrated circuit), a reduced instruction set computer, an analog computer, a digital computer, a molecular computer, a quantum computer, a cellular computer, a superconducting computer, a supercomputer, a solid-state computer, a single-board computer, a buffered computer, a computer network, a desktop computer, a laptop computer, a scientific computer, a scientific calculator, or a hybrid of any of the foregoing. More specifically, the controller 6 is a microprocessor coupled to a ROM (read only memory).

The information received by the controller 6 is electronic information, such as a signal or the like, or more specifically, resonant complex impedance, complex impedance, electrochemically-modulated complex impedance, electrical current, and/or any other electrical information that sufficient to provide the controller 6 the ability to determine the concentration of contaminants within the liquid 8. In general, the information will be received in analog form. If so, the sampling frequency should be greater than about 0.0001 hertz (Hz), more specifically, greater than about 1.0 Hz, and, even more specifically, greater than about 100.0 Hz. In one example, the controller can receive information at about 400 Hz. The information can also be received in digital form and/or be converted by the controller into digital form (e.g., utilizing an analog to digital converter).

To determine the concentration of a contaminant in the liquid 8, the controller 6 can compare the information received from the sensors/sensor arrays to memory (e.g., a look-up table, a data array, a calibration curve, and so forth). The memory accessed by the controller 6 is desirably programmed by the manufacturer based upon experimental test results, however can be empirically determined by the controller 6 or user (e.g., anyone operating the CDS). The memory can be connected in operational communication to the controller 6 or integral therein.

The operations employed by the controller 6, can be embodied in the form of computer-implemented processes and/or other apparatuses for practicing the processes. These operations can also be embodied in the form of computer program code containing instructions embodied in tangible media, such as floppy diskettes, CD-ROMs, hard drives, or any other computer-readable storage medium, wherein, when the computer program code is loaded into and executed by a computer or controller, the computer becomes an apparatus for practicing the method. The methods may also be embodied in the form of computer program code or signal, for example, whether stored in a storage medium, loaded into and/or executed by a computer or controller, or transmitted over some transmission medium, such as over electrical wiring or cabling, through fiber optics, or via electromagnetic radiation, wherein, when the computer program code is loaded into and executed by a computer, the computer becomes an apparatus for practicing the method. When implemented on a general-purpose microprocessor, the computer program code segments configure the microprocessor to create specific logic circuits.

To be most specific, the technical effect of the actions of the controller 6 is to evaluate electrical information acquired from a sensor and/or sensor array and determine a contaminant concentration within a liquid 8. When these capabilities are embodied in software, firmware, hardware or some combination thereof, the embodiment can be an individual article for sale or included as a part of a computer system or sold separately.

Figure 7:
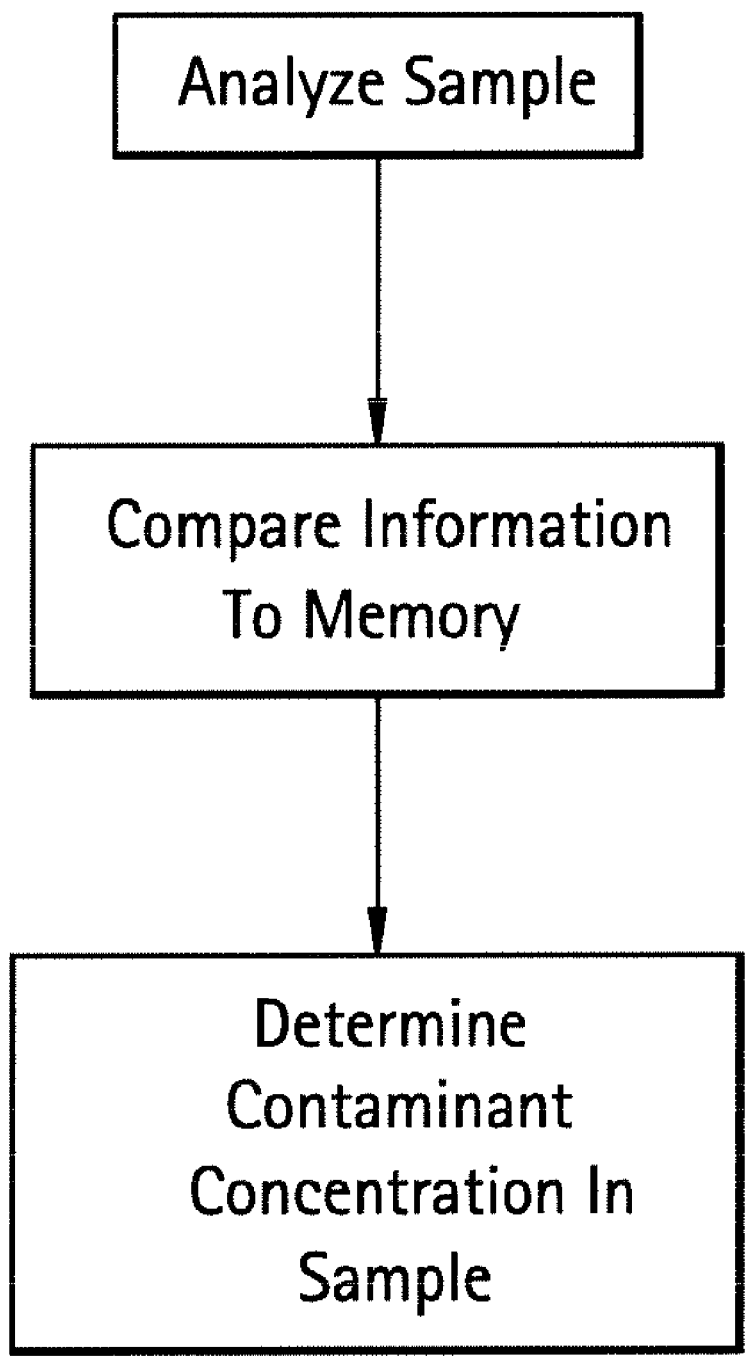
FIG. 7 is illustrates an exemplary method for operating the contaminant detection system (CDS).

The contaminant detection system (CDS) 2 can be operated by the exemplary method illustrated in FIG. 7, wherein the method comprises: analyze a liquid, compare information to memory, and determine the contaminant concentration within the liquid. A liquid 8 can be analyzed by a sensor 4, 40, or sensor array 50, 60, that is disposed in fluid communication with the liquid 8. For example, in a nuclear reactor (e.g., a nuclear power plant), a sensor array 60 can be disposed directly on a pipe comprising cooling water (the liquid 8), whereby the cooling water can be directly analyzed without any additional operations. However, in an alternative embodiment, the liquid 8 can be sampled using a pipette, or other sampling means, and disposed in fluid contact with the sensor 4, 40 and/or sensor array 50, 60. It is also noted that any number of sensors can be employed, which can be disposed in any numerous configurations and provide differing types of information (e.g., temperature, pressure, flow rate, and so forth).

Figure 8:
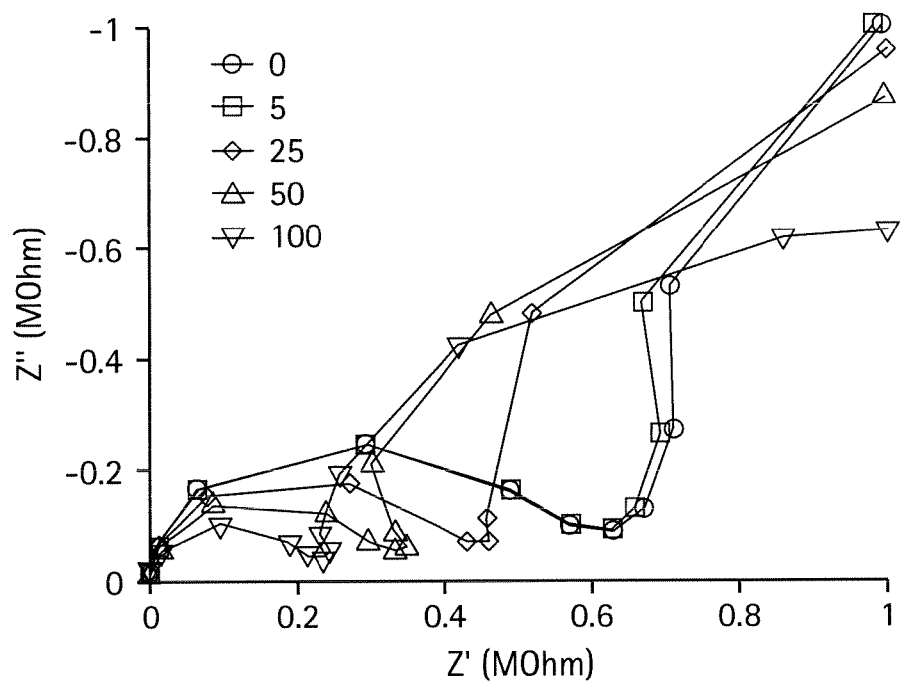
FIG. 8 is an illustration of an exemplary complex impedance graph.

During the analysis of the liquid 8, the controller 6 receives electrical information (e.g., resonant complex impedance, complex impedance, electrochemically-modulated complex impedance, and/or electrical current) from the sensor(s) 4, 40 and/or sensor array(s) 50, 60. For example, referring now to FIG. 8, an exemplary illustration of a complex impedance graph is illustrated. On the x-axis, Z' is illustrated in mega-ohms, wherein Z' is the real part of complex impedance. On the y-axis, Z" is illustrated in mega-ohms, wherein Z" is the imaginary part of complex impedance. As can be seen in the graph, five data plots are illustrated. The first plot, labeled Sample 1, comprised water having 0 parts per billion by weight (ppb) chloride ions. The second plot, labeled Sample 2, comprised water having 5 ppb chloride ions. The third plot, labeled Sample 3, comprised water having 25 ppb chloride ions. The fourth plot, labeled Sample 4, comprised water having 50 ppb chloride ions, and the fifth plot, labeled Sample 5, comprised water having 100 ppb chloride ions. As can be seen from the data, the various plots exhibited marked differences in impedance responses, and can therefore be utilized to quantify the concentration of the contaminant within the sample.

Figure 9:
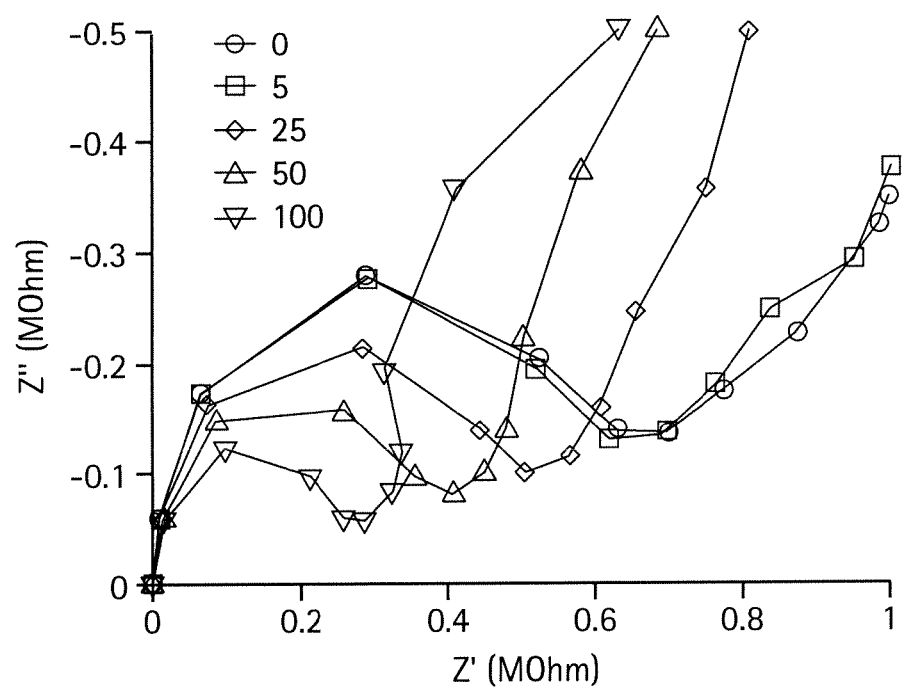
FIG. 9 is an illustration of an exemplary complex impedance graph.

Referring now to FIG. 9, another exemplary illustration of a complex impedance graph is illustrated. On the x-axis, Z' is illustrated in mega-ohms, wherein Z' is the real part of complex impedance. On the y-axis, Z" is illustrated in mega-ohms, wherein Z" is the imaginary part of complex impedance. As can be seen in the graph, five data plots are illustrated. The first plot, labeled Sample 1, comprised water having 0 ppb sulfate ions. The second plot, labeled Sample 2, comprised water having 5 ppb sulfate ions. The third plot, labeled Sample 3, comprised water having 25 ppb sulfate ions. The fourth plot, labeled Sample 4, comprised water having 50 ppb sulfate ions, and the fifth plot, labeled Sample 5, comprised water having 100 ppb sulfate ions. Again, the various plots exhibit marked differences in impedance responses, which allows the graphs to be employed to quantify the concentration of the contaminant within the sample.

Figure 10:
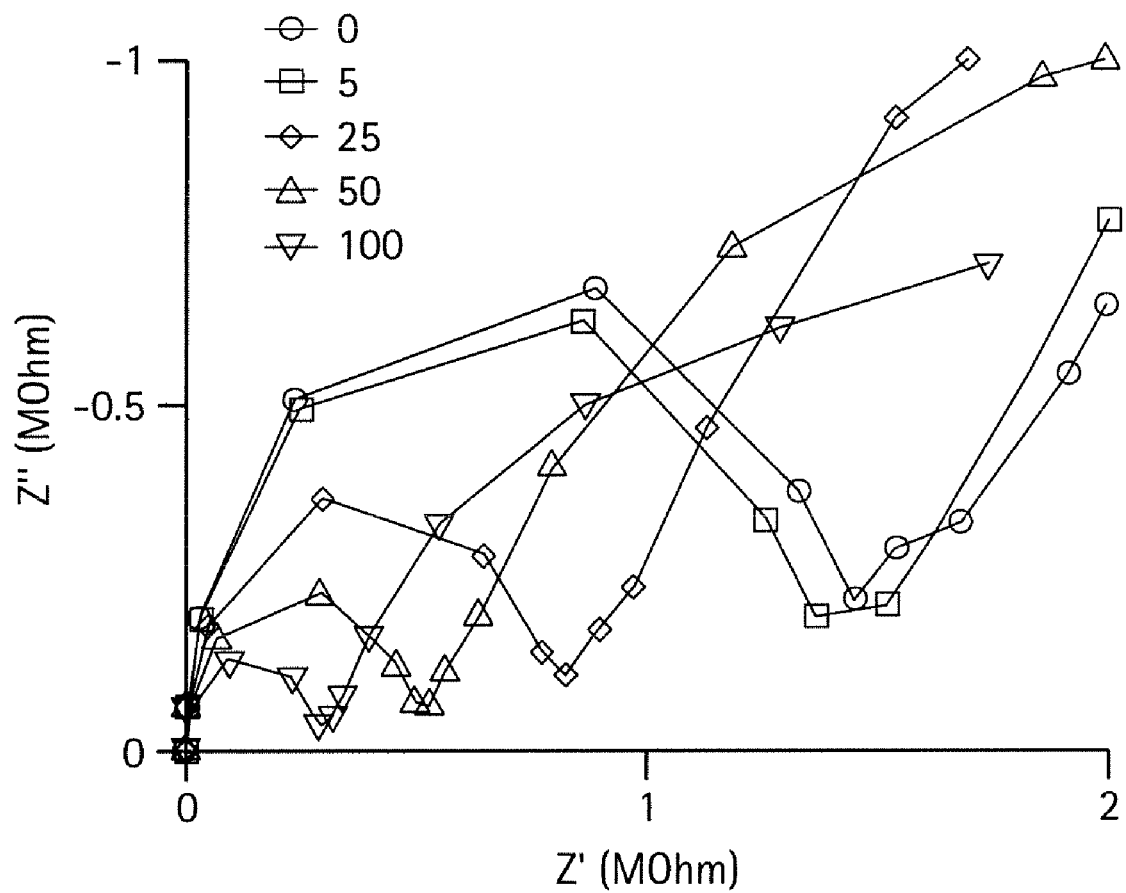
FIG. 10 is an illustration of an exemplary complex impedance graph.

Referring now to FIG. 10, yet another exemplary illustration of a complex impedance graph is illustrated. On the x-axis, Z' is illustrated in mega-ohms, wherein Z' is the imaginary part of complex impedance. On the y-axis, Z" is illustrated in mega-ohms, wherein Z" is the real part of complex impedance. As can be seen in the graph, five data plots are illustrated. The first plot, labeled Sample 1, comprised water having 0 ppb zinc ions. The second plot, labeled Sample 2, comprised water having 5 ppb zinc ions. The third plot, labeled Sample 3, comprised water having 25 ppb zinc ions. The fourth plot, labeled Sample 4, comprised water having 50 ppb zinc ions, and the fifth plot, labeled Sample 5, comprised water having 100 ppb zinc ions. As can be seen yet again, the various plots exhibited marked differences in impedance responses. Therefore, the responses can be utilized to quantify the concentration of the contaminant within the sample.

Upon receiving the information, it can be conditioned utilizing filters (e.g., bandwidth filters, voltage filters, and sampling filters), converters (e.g., analog to digital converters), signal processors (e.g., Fourier waveform processors, wavelet transform processors, and so forth), buffers, and so forth.

Regardless of conditioning, the information can be stored in memory (e.g., random access memory) for comparison to known information in the next step of the method.

Once the controller 6 has received information from the sensor(s) 4, 40 and/or sensor array(s) 50, 60, the controller 6 advances to the second step, wherein the information is compared to known information stored in memory (e.g., a look-up table, data array, calibration curve, and so forth). During the comparison, aspects of the information received are compared to known information to then provide the controller 6 with any additional information needed to determine the concentration of a specific contaminant within the liquid 8. The aspects of the information can be specific characteristics such as peak amplitude, frequency, phase, and so forth. In one example, a controller receives impedance information from a sensor 40 and temperature information from a thermocouple disposed in fluid communication with the purge chamber 42 of the sensor 40, wherein the impedance is 55 kilo-ohms and the temperature is 27° C. From this information, the controller 6 can reference a look-up table, such as that illustrated in FIG. 11 and determine that the temperature plot will be interpolated between the 20° C. plot and the 30° C. plot, with respect to an algorithm (the impedance response in the exemplary embodiment is a logarithmic function of temperature), to provide a 27° C. plot from which the corresponding concentration can be determined. At this point, the controller 6 can advance to the third step of the method wherein the concentration of the contaminant is determined.

Figure 11:
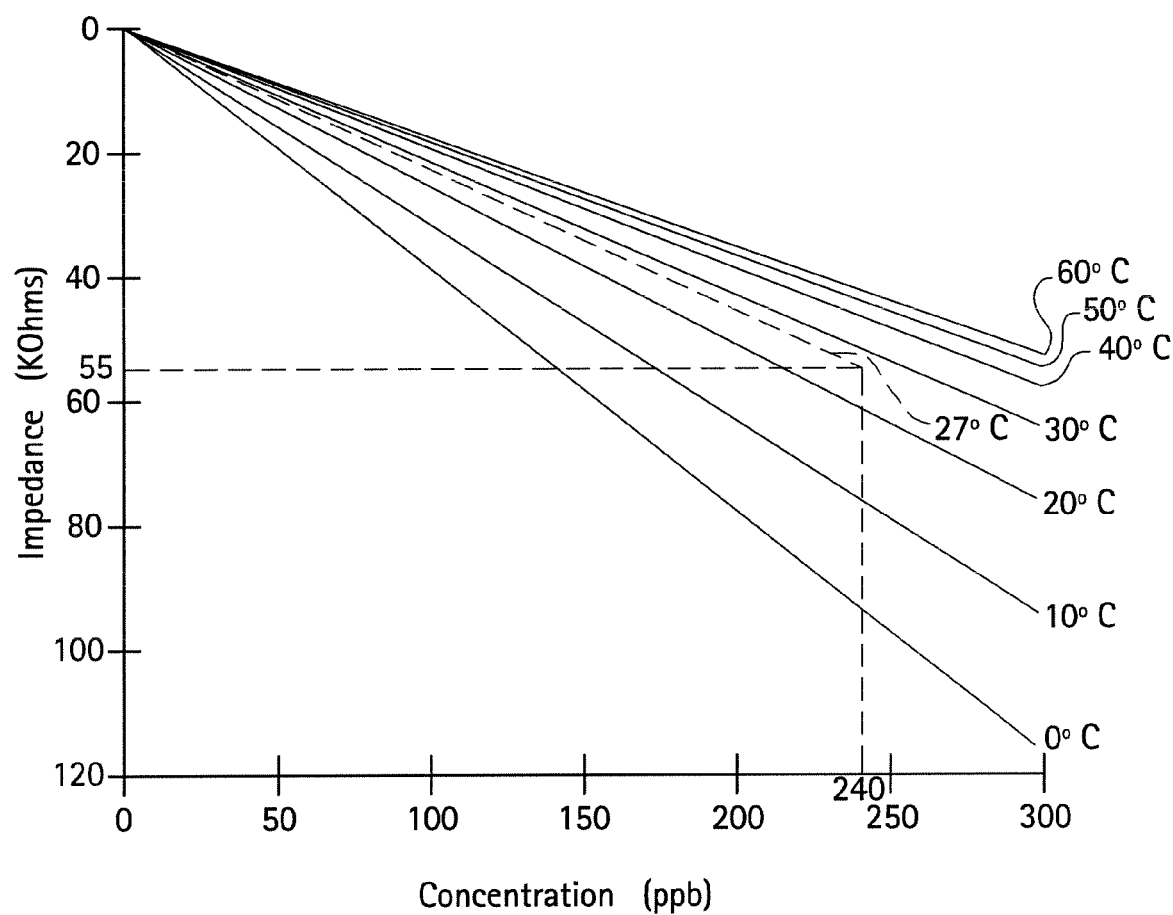
FIG. 11 is an exemplary graphical look-up table.

In the third step of the method, the controller 6 utilizes any information accessed from memory to determine the contaminant concentration within the liquid 8. The concentration can be calculated utilizing algorithms, interpolation, extrapolation, calculations, and any other technique, as well as correlated based on information gathered by, or known by, the controller 6. For example, continuing with the example above, once the controller 6 has determined that the 27° C. plot is to be interpolated from the 20° C. and the 30° C. data plots, the 27° C. plot is interpolated and utilized to determine at 27° C. and 55 kilo-ohms the corresponding concentration is 240 parts per billion (ppb), as illustrated in FIG. 11.

In addition, at any step of the exemplary method the controller 6 can determine if the information received is acceptable to utilize to determine the concentration of the contaminant of interest in the liquid 8. For example, during the second step of the method wherein the information received is compared to memory, the controller 6 can receive additional information, such as from an additional sensor 40 in the sensor array 50 or from the second transducer 92 in sensor 60, wherein the additional information can be utilized to determine if a high concentration of an non-desired contaminant has adversely affected the information or can be employed to account for the specific concentration of the non-desired contaminant.

In an alternative embodiment, the controller 6 can be capable of employing multivariate analysis tools to quantify the concentrations from the electrical information, such as canonical correlation analysis, regression analysis, principal components analysis, discriminant function analysis, multidimensional scaling, linear discriminant analysis, logistic regression, and/or neural network analysis.

Multivariate analysis tools are especially applicable wherein a sensor array 50, 60 is employed since the amount of electrical information received by the controller 6 can be massive. To that end, multivariate analysis tools offer several advantages over univariate calibration methods. Firstly, signal averaging is achieved since more than one measurement channel is employed in the analysis. Also, the concentrations of multiple species may be measured if they are present in the calibration liquid. A calibration model is built by using responses from calibration standard solutions. The analysis of unknown liquids will suffer if a species is present in the liquid that is not accounted for in the calibration model. This is mitigated somewhat by the ability to detect whether a liquid is an outlier from the calibration set. Multivariate calibration approaches permit selective quantitation of several species of interest in a liquid (e.g., water) that has multiple species (e.g., contaminants) and interferences using low-resolution instruments such as sensors 4 with sensing films 12 when overlapping responses from different species preclude the use of univariate analysis.

In one embodiment, principal components analysis (PCA) was used to extract the desired descriptors from the dynamic data. PCA is a multivariate data analysis tool that projects the data set onto a subspace of lower dimensionality with removed co-linearity. PCA achieves this objective by explaining the variance of the data matrix X in terms of the weighted sums of the original variables with no significant loss of information. These weighted sums of the original variables are called principal components (PCs). Upon applying the PCA, the data matrix X is expressed as a linear combination of orthogonal vectors along the directions of the principal components:

$$X = t_1 p^T_1 + t_2 p^T_2 + \ldots + t_A p^T_K + E \quad \text{(Equation 1)}$$

where: t is the score
p are the loading vectors
K is the number of principal components,
E is a residual matrix that represents random error, and
T is the transpose of the matrix.

Prior to PCA, data was appropriately preprocessed, such as by auto scaling.

Figure 12:
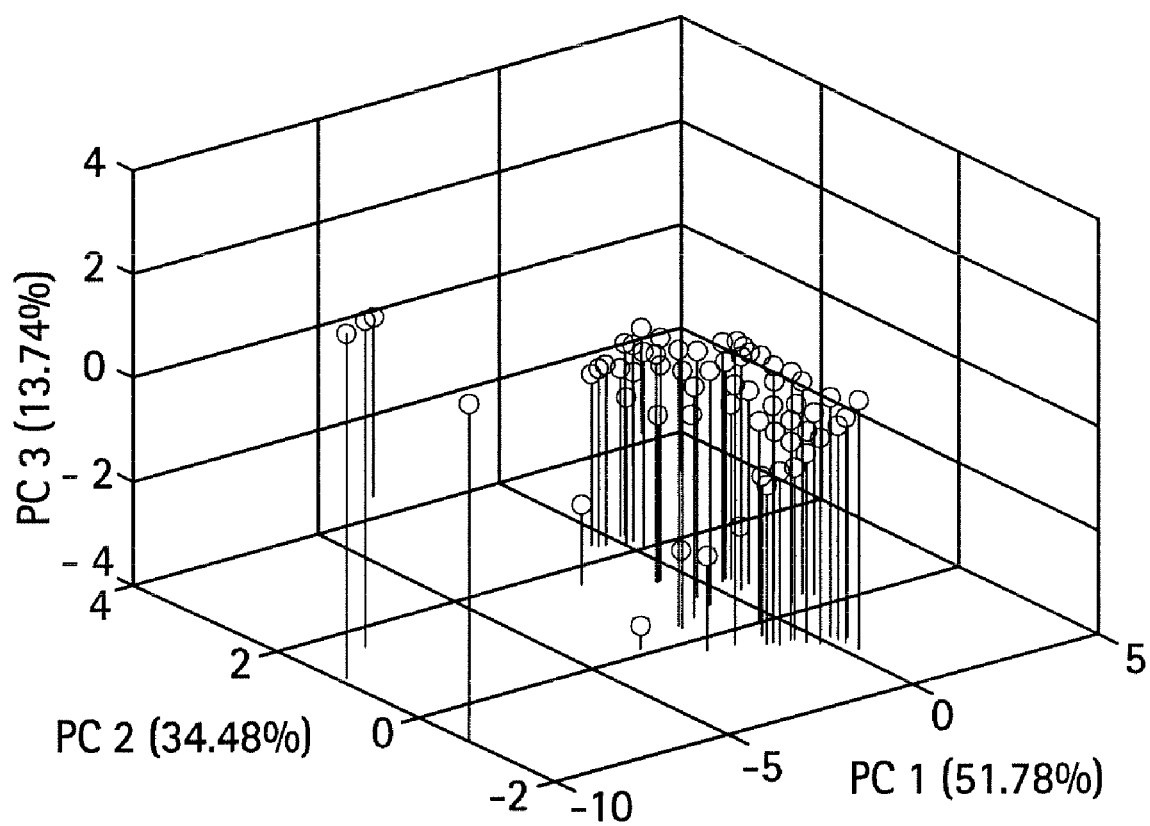
FIG. 12 is an exemplary illustration of a partial component analysis (PCA) graph.
Figure 13:
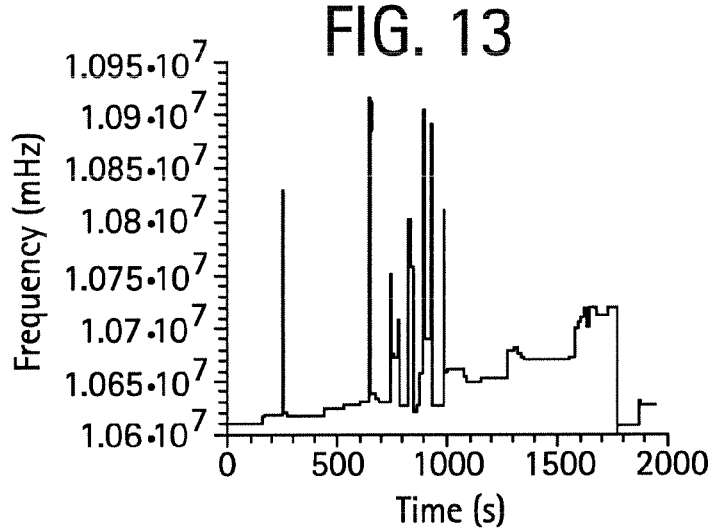
FIG. 13 is an exemplary illustration of a frequency shift graph.
Figure 14:
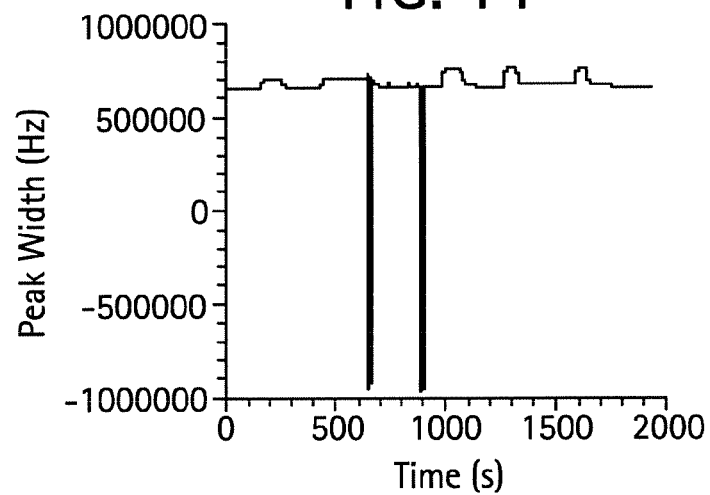
FIG. 14 is an exemplary illustration of a peak width of imaginary signal component graph.
Figure 15:
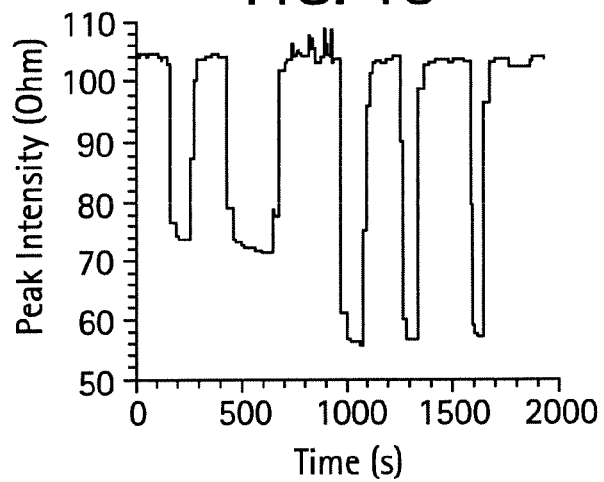
FIG. 15 is an exemplary illustration of a peak intensity of the real signal component graph.

To demonstrate the applicability of multivariate analysis, a passive RFID sensor with a nominal frequency of 13.56 megahertz (MHz) was immersed into pure water. Variable concentrations of NaCl were made and the RFID sensor was put in contact with about 600 and 1,000 ppb of NaCl. Exposures were made in several replicates. Measurements were performed using a network analyzer that measured three parameters from the wireless sensor including frequency shift, peak width, and peak intensity, as shown in FIGS. 13, 14, 15, respectively. Results of multivariate analysis are depicted in FIG. 12, wherein a scores plot of three principal components of dynamic data shows a complex relation between measured signals from one RFID sensor. The relationships in the collected data were described by plotting scores of relevant principal components (e.g., PC 1, PC 2, and PC 3) of the PCA model versus each other, processing the data shown in FIGS. 13-15 using Equation 1.

Figure 16:
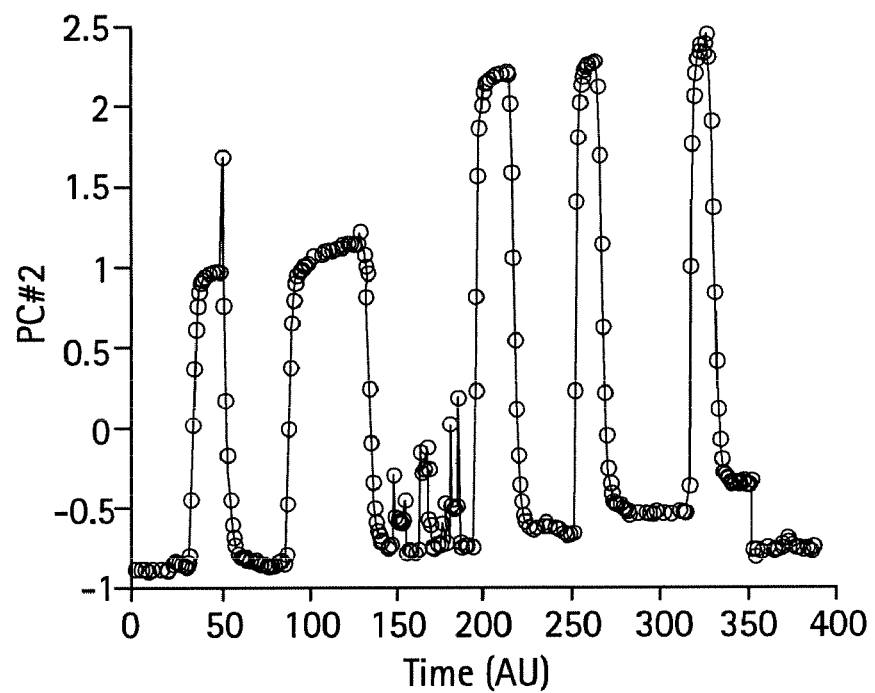
FIG. 16 is an exemplary illustration of a second principal component as a function of experimental time graph.
Figure 17:
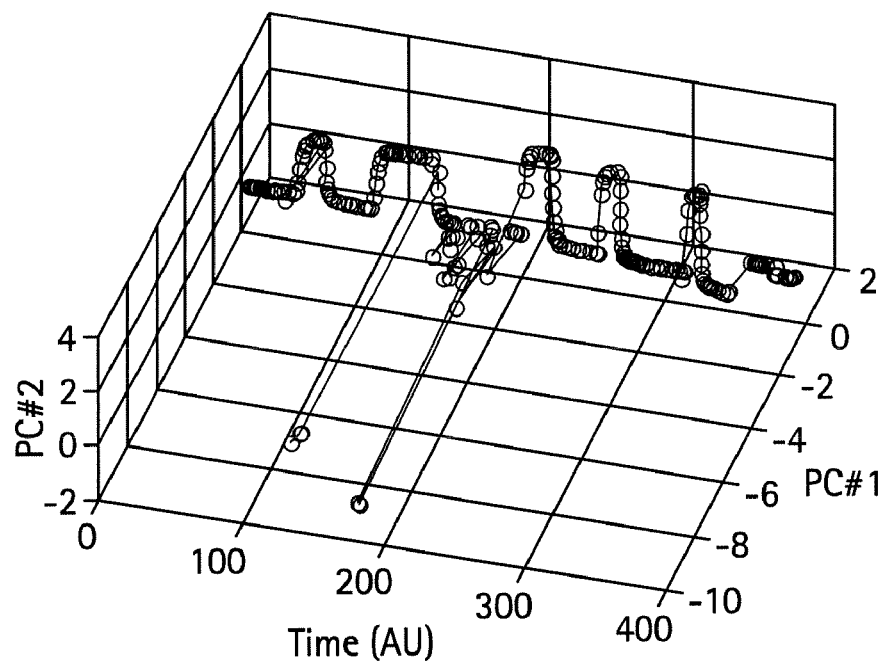
FIG. 17 is an exemplary illustration of first and second principal components as a function of experimental time graph.

To be even more specific, the data was communicated to a controller 6 using a wireless RFID transducer that measured complex impedance comprising a real part and imaginary part. Non-limiting examples of these measured parameters include shift of the maximum of the real part of the complex impedance, peak width of the complex impedance, and magnitude of the real part of the complex impedance (peak intensity). Multivariate analysis permits an identification of main factors affecting the response of the sensor and relating to the response and interferences. For example, referring now to FIG. 16, an exemplary graph illustrates PCA results showing a plot of second principal component (PC) as a function of experimental time depicting the results from two replicate exposures to about 600 ppb NaCl and three replicate exposures to about 1,000 ppb NaCl. However, based on the response of a single PC, it is difficult to determine the effects on the sensor. Thus, a combination of several responses of the wireless sensor is analyzed. For example, referring now to FIG. 17, an exemplary graph shows PCA results of first and second PCs as a function of experimental time depicting the results from two replicate exposures to about 600 ppb NaCl and three replicate exposures to about 1,000 ppb NaCl. Clearly, analysis of more than one response from a single sensor provides a desired discrimination between noise contributions and useful signal.

To ensure the quality of the wireless sensor data analyzed using multivariate tools, such as PCA, several statistical tools may be applied. These tools are multivariate control charts and multivariate contributions plots. Multivariate control charts use two statistical indicators of the PCA model, such as Hotelling's $T^2$ and Q values plotted as a function of combinatorial sample or time. The significant principal components of the PCA model are used to develop the $T^2$-chart and the remaining PCs contribute to the Q-chart. The sum of normalized squared scores, $T^2$ statistic, gives a measure of variation within the PCA model and determines statistically anomalous samples:

$$T^2_i = t_i \lambda^{-1} t_i^T = x_i P \lambda^{-1} P^T x_i^T \qquad \text{(Equation 2)}$$

where: $t_i$ is the $i^{th}$ row of Tk, the matrix of k scores vectors from the PCA model, $\lambda^{-1}$ is the diagonal matrix containing the inverse of the eigenvalues associated with the K eigenvectors (principal components) retained in the model, $x_i$ is the $i^{th}$ sample in X, and P is the matrix of K loadings vectors retained in the PCA model (where each vector is a column of P).

The Q residual is the squared prediction error and describes how well the PCA model fits each sample. It is a measure of the amount of variation in each sample not captured by K principal components retained in the model:

$$Q_i = e_i e_i^T = x_i (I - Pk\, Pk^T) x_i^T \qquad \text{(Equation 3)}$$

where: $e_i$ is the $i^{th}$ row of E, and

I is the identity matrix of appropriate size (n×n).

Figure 18:
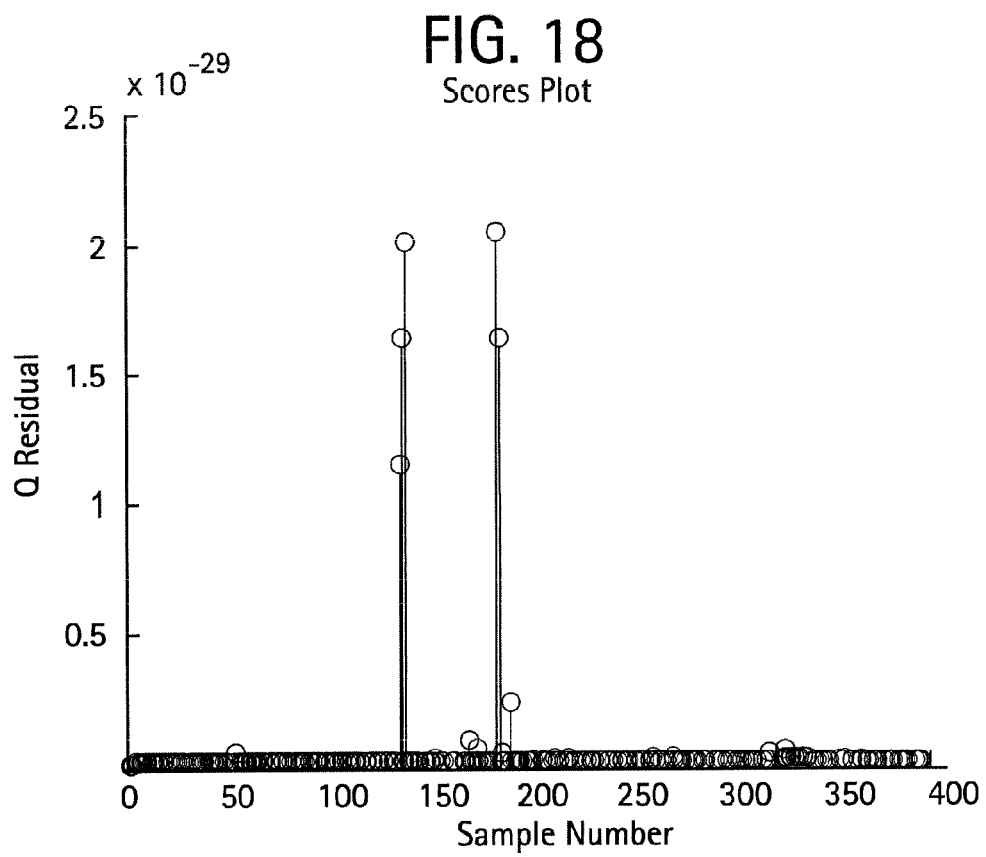
FIG. 18 is an exemplary illustration of a multivariate Q-residual statistics control chart graph.
Figure 19:
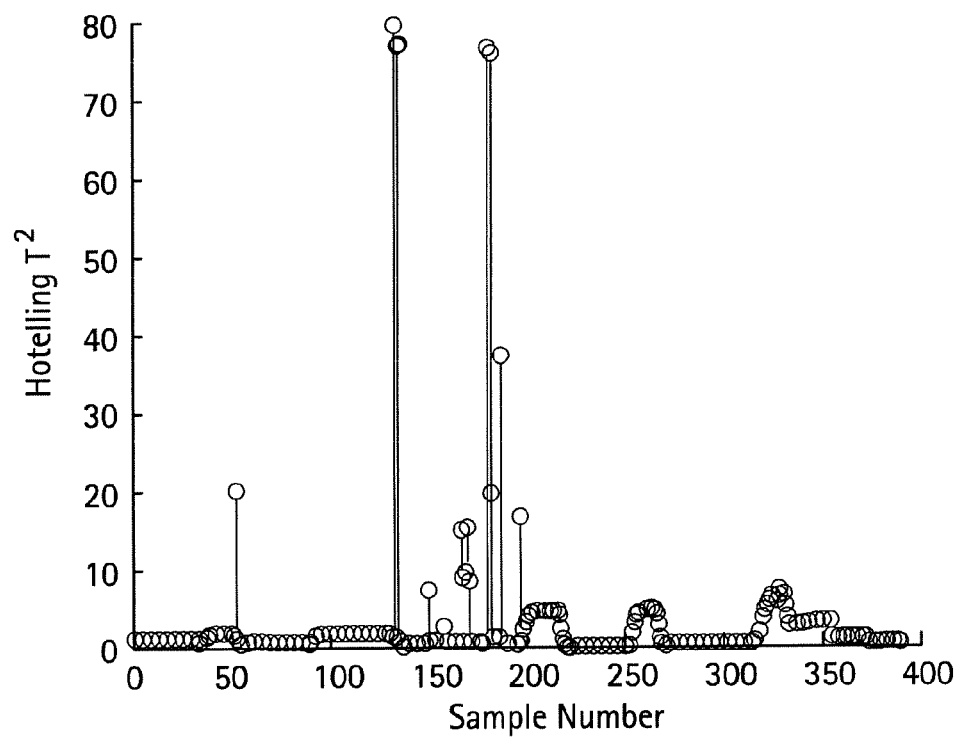
FIG. 19 is an exemplary illustration of a multivariate Hotelling-$T^2$ statistics control chart graph.

Referring to FIG. 18 and 19, exemplary multivariate Q and T2 statistics control charts for the dynamic data from the wireless sensor are presented, respectively. These control charts illustrate that several data points exceed the 95% confidence limits for the T2 and Q statistics described by the PCA model. The contributions plots of these statistical parameters can be used to track the origin of the largest contributors to these alarms.

Over time, the chemical sensor response can drift and lead to erroneous results. Therefore, compensation for the drift can enhance the sensor long-term performance and enable accurate results. An embodiment of using the chemical sensor, therefore, comprises introducing a liquid to the sensor, contacting the chemical probe (i.e., chemical sensor) and a conductivity probe (i.e., conductivity sensor) to determine the concentration of a particular species (e.g., ion) in the liquid, as well as the conductivity (e.g., microSiemens per centimeter) for that liquid at that time. The chemical concentration measurements can then be corrected (e.g., adjusted) by the conductivity measurements to compensate for the drift, as the conductivity of the solution will be changed non-selectively by the addition of any species to the solution. This correction is possible in any type of liquid so long as the conductivity probe (conductivity sensor) has sufficient sensitivity to measure a change in conductivity of the liquid over time (e.g., depending upon the sensitivity of the sensor and the noise). Hence, the sensor can comprise chemical probe(s) (i.e., chemical sensor(s); e.g., the sensor array), conductivity probe(s) (i.e., conductivity sensor(s)), and, optionally, temperature probe(s) (i.e., temperature sensor(s)), wherein, as with the chemical probe, the conductivity probe is in fluid communication with the liquid to enable a conductivity determination. For example, a first conductivity probe can be located in liquid 8 (e.g., to measure conductivity in the liquid 8), and/or a second conductivity probe can be located in chamber 42 to measure conductivity in the liquid in chamber 42.

The conductivity probe can provide measurements of conductivity obtained in the DC mode. The conductivity sensor provides measurements of conductivity at multiple frequencies where complex impedance measurements are performed to obtain real and imaginary parts of the complex impedance.

The correction from the response of the conductivity and/or the temperature probe can be performed by a multivariate correction. Multivariate correction for conductivity changes is performed where conductivity is measured at different frequencies and Z' and Z" values (described above) are obtained at these different frequencies. The measured frequency range can be 0.00001 Hz to 100,000,000 Hz (i.e., 100 MHz), or more specifically, 0.0001 Hz to 10 MHz, and even more specifically, 0.001 Hz to 5 MHz. These multifrequency conductivity responses are further combined with the response of the chemical sensor, or sensor array, using multivariate analysis tools by combining a data matrix from the conductivity probe and the data matrix from chemical sensor and doing multivariate analysis on the resulting combined matrix using the multivariate analysis tools are described above. Optionally, correction from the conductivity sensor can be performed by a univariate correction. A nonlimiting example of univariate correction is when the response from chemical sensor is normalized by the response of the conductivity sensor.

In one embodiment, chemical sensor drift correction is performed by a comparative correction. When a chemically induced change in the conductivity response is measured that exceeds a preset conductivity threshold, a chemical sensor measurement is performed. The chemical sensor measurement is the difference between the chemical sensor response before the threshold change in the conductivity sensor response and the chemical sensor response after the threshold change in conductivity sensor response. The threshold conductivity response is an arbitrary value that can be calculated or specified at various temperatures for specified detection limits when the baseline conductivity is known. For example, ultrapure water at 25° C. has a conductivity of 0.055 µS/cm. The threshold value to perform a chemical sensor measurement could be chosen to be, for example, 0.1 µS/cm (when the impurities present in the water caused the conductivity to exceed 0.1 µS/cm, a chemical sensor measurement would be performed). As the differential chemical sensor measurement is performed over short periods of time, the effect of drift should be minimized. Drift that occurs without a corresponding change in conductivity will be ignored.

The temperature probe can be disposed in thermal communication with the liquid so as to enable a temperature determination to be obtained. Since, the responses of the conductivity probe and the chemical sensor are temperature dependent, temperature corrections can also be done on the readings, with the temperature corrections being linear or nonlinear. In addition to the conductivity data matrix, temperature data can also be added for the data analysis and compensation for temperature affects.

It is further noted that correction can be made for surface and bulk effects of the film. To correct for surface and bulk effects in the sensor films, an identical sensor film composition is deposited into a working chemical sensor and onto a control sensor. The working chemical sensor measures a signal as described above. The control chemical sensor measures the complex impedance signal similar to that shown in FIGS. 8-10, but obtained when the transducer is coated with the control sensing film. The bulk dielectric property of the film that is related to the leaching of the film components, other irreversible changes in the film (such as incomplete diffusion of species from the film upon exposure to chemicals) and sensor film thickness, is determined from the relatively high frequency response, while the surface effects (e.g., such as surface contamination of the film and erosion of the film) are determined from the relatively low frequency response.

The following examples are merely exemplary and are provided to further illustrate the sensor and the use thereof and are not intended to be limiting.

EXAMPLES

Experiment 1

In the first experiment, a sensor 2 was constructed using a radio frequency identification tag as a transducer 10 (operating at nominal frequency of 13.56 MHz) and a polysulfone film 12. The RFID transducer was purchased from Digi-Key, under part number 481-1067-1-ND.

The sensor was assembled by dissolving polysulfone in dimethyl sulfoxide (DMSO, purchased from Aldrich Chemical Company Inc.) at 37° C. for 24 hours to produce a solution having about 10%-15% solids by volume. A coating was then applied to the RFID transducer and allowed to dry at 37° C. for 24 hours. After the coating was dry, the resulting film 12 had an average thickness of about 50 micrometers.

The polysulfone-coated sensor 2 was disposed within the conduit of a test apparatus. For comparison, an uncoated transducer 10 was also disposed within the conduit. A data acquisition system (LabVIEW, National Instruments, Inc) was operably connected to the sensor 2 and uncoated transducer 10 such that the Zmax could be recorded as the sensor 2 and the uncoated transducer 10 were subjected to various solutions comprising varying chemical contaminants at various concentrations.

The Zmax and magnitude of the real part of the complex impedance (peak intensity) of the polysulfone-coated sensor 2 and the uncoated transducer 10 were measured as a first aqueous solution comprising about 100 ppb NaSO4 was passed through the conduit. When the Zmax values appeared to plateau, water was passed through the conduit to purge the ions from the film 12. This procedure was repeated using a second aqueous solution comprising about 100 ppb HCl, a third aqueous solution comprising about 100 ppb NaCl, and a fourth aqueous solution comprising about 100 ppb KH2PO4.

Figure 20:
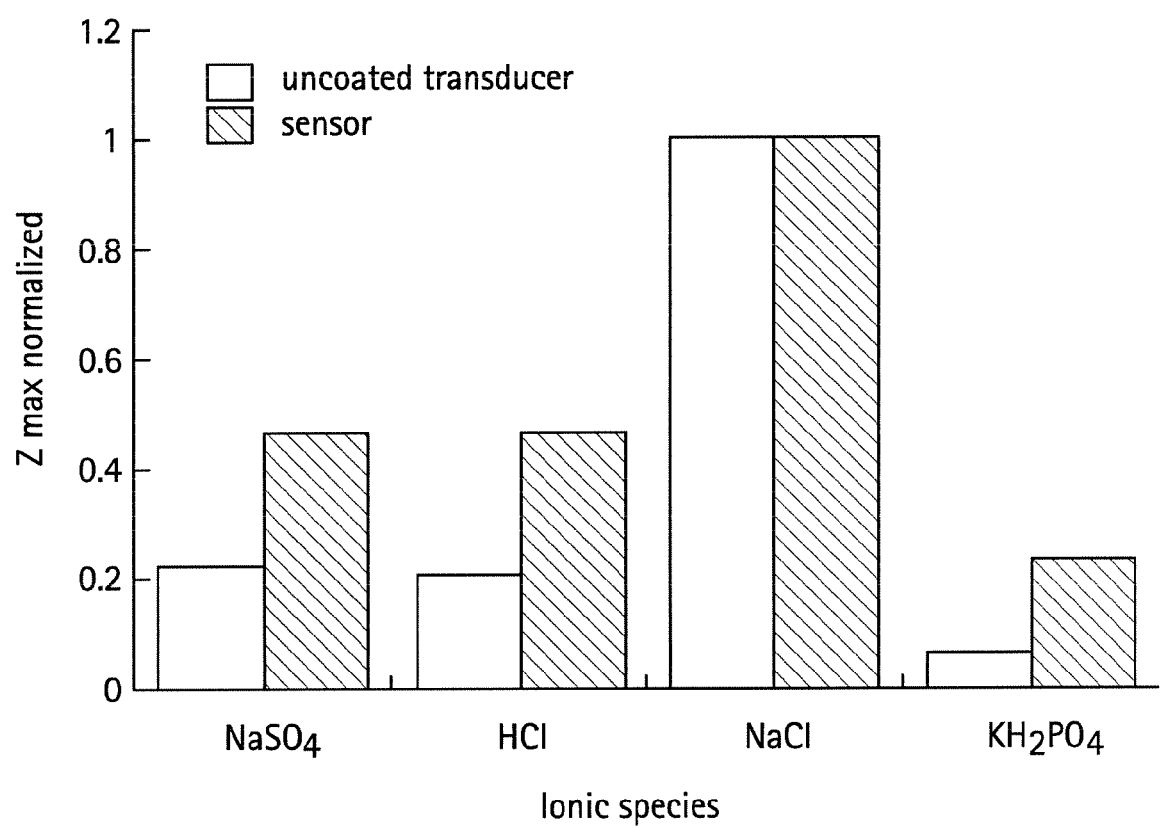
FIG. 20 is an exemplary graphical representation selectivity and sensitivity responses generated during Experiment 1 for a transducer.

Illustrated in FIG. 20 is the exemplary graph generated during Experiment 1. As can be seen, the Z max responses of the uncoated RFID transducer and the polysulfone coated RFID transducer 10 were normalized by the respective responses to NaCl. This signal normalization was performed to assess the diversity of the response of the sensors to four different ionic solutions when the transducer is uncoated and coated with the sensing film 12 (polysulfone). As shown, the response patterns for four solutions obtained with uncoated and coated transducers are different as desired for the application of this approach for differentiation between the different ionic solutions.

Experiment 2

In a second experiment, a sensor 2 was constructed using a radio frequency identification tag as a transducer 10 (operating at nominal frequency of 13.56 MHz) and a poly(hydroxyethylmethacrylate) film 12. The sensor was assembled by dissolving poly(hydroxyethylmethacrylate) (Aldrich Chemical Co.) in 1-methoxy-2-propanol (Aldrich) at 20° C. for 24 hours to produce a solution having about 10%-15% solids by volume. A coating was then applied to the RFID transducer and allowed to dry at 20° C. for 24 hours. The resulting film 12 had an average thickness of about 10-50 micrometers.

The poly(hydroxyethylmethacrylate) coated sensor was disposed in a test apparatus similar to that utilized in Experiment 1 and Experiment 2, however an uncoated transducer was not employed. The apparatus was capable of measuring the Zmax of the poly(hydroxyethylmethacrylate) coated sensor 2 with respect to time.

The poly(hydroxyethylmethacrylate) coated sensor was subjected to a first aqueous solution comprising 40 ppb NaCl. When the Zmax value appeared to plateau, water was introduced to purge the ions from the film 12. Thereafter a second aqueous solution comprising 8 ppb NaCl was passed through the conduit. When the Zmax value appeared to plateau, water was introduced to purge the ions from the film 12. Thereafter, a third aqueous solution comprising 14 ppb HCl was passed through the conduit. When the Zmax value appeared to plateau, water was introduced to purge the ions from the film 12. Thereafter, a fourth aqueous solution comprising 72 ppb HCl was passed through the conduit. When the Zmax value appeared to plateau, water was introduced to purge the ions from the film 12.

Figure 21:
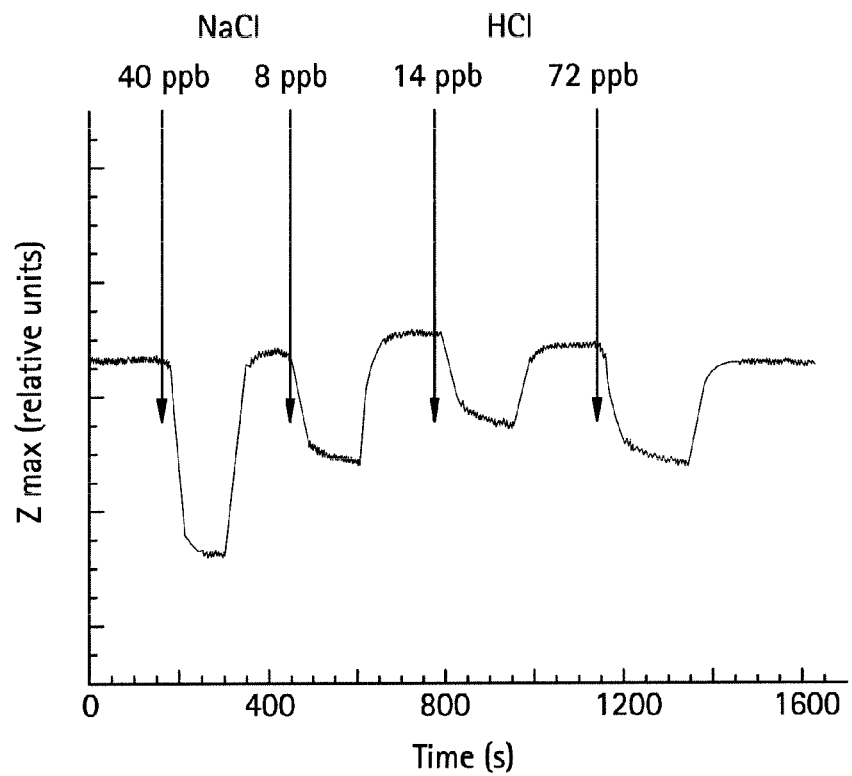
FIG. 21 is an exemplary graphical representation selectivity and sensitivity responses generated during Experiment 2 for a transducer.

Illustrated in FIG. 21 is the exemplary graph that illustrates the results of Experiment 2, wherein the graph shows that the Zmax value starts at that of water. As indicated, when the first solution is introduced, at about 200 seconds, the Zmax begins to decrease as a result of the ions passing into the film 12. At about 300 seconds, the Zmax reaches a plateau, whereat water was introduced into the conduit to flush the NaCl ions form the film 12. As is noticed, again the Zmax returned to about that of water. At about 425 seconds, the second solution was added, and the Zmax began to decrease and reached a plateau at about 600 seconds. It is noted that the plateau of the second solution does not exhibit the Zmax value of the first solution, therefore, the sensor 2 is capable of providing a Zmax that is dependent upon concentration. This can also be seen when comparing the Zmax of the third solution to that of the fourth solution. In addition, the NaCl generally exhibits a greater Zmax value than that of HCl (comparing 8 ppb NaCl to 14 ppb HCl, and 40 ppb NaCl to 72 ppb HCl), hence the amount of NaCl ions that migrated into the film 12 is greater than the amount of HCl ions allowed to pass. Further, it is noted that with the water purge between sampling, the measured Zmax returns to about baseline.

Experiment 3

In a third experiment, a sensor 2 was constructed using a two-electrode gold interdigitated transducer 10 (see FIG. 3) and a polyaniline (PANI) film 12. The aniline monomer was purchased from Aldrich Chemical Company Inc., under part number 242284

The polymer film 12 was deposited by electropolymerizing the aniline monomer on the surface of the transducer at a concentration of 0.1 M aniline in 1 M $H_2SO_4$ under a cycling applied potential between −0.3 V and 1.1 V versus a silver/silver chloride reference at a rate of 50 mV per second. The resulting polyaniline film 12 had an average thickness of about 1 to about 100 micrometers.

The polyaniline coated sensor 4 was connected to a data acquisition system operated using LabVIEW, National Instruments and subjected to an aqueous solution comprising 40 ppb ZnCl. When the impedance appeared to plateau, water was introduced to purge the ions from the film 12. Thereafter a second aqueous solution comprising 190 ppb ZnCl was passed through the conduit. When the impedance appeared to plateau, water was introduced to purge the ions from the film 12. Thereafter, a third aqueous solution comprising 151 ppb ZnCl was passed through the conduit. When the impedance appeared to plateau, water was introduced to purge the ions from the film 12.

Figure 22:
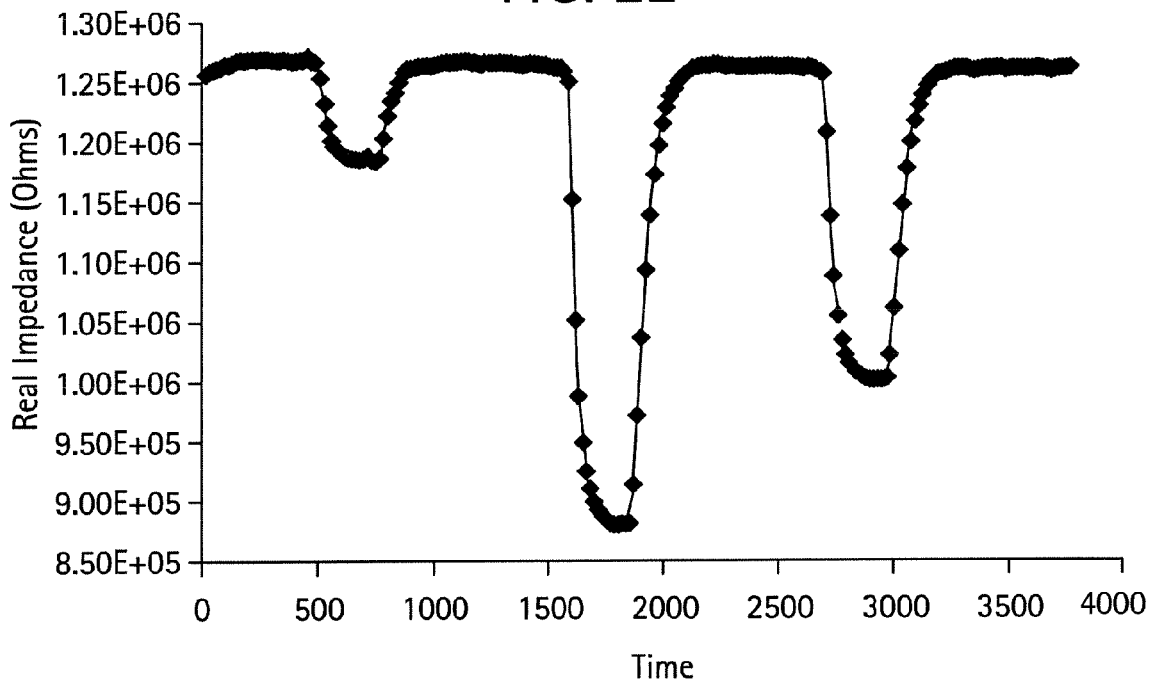
FIG. 22 is an exemplary graphical representation selectivity and sensitivity responses generated during Experiment 3 for a transducer.

In FIG. 22 an exemplary graph illustrates the results of Experiment 3, wherein the graph shows real impedance in ohms with respect to time. The plot starts at an impedance signal of the sensor in water (e.g., about $1.127 \times 10^6$ ohms). At about 500 seconds the first solution is introduced and the impedance decreases to about $1.175 \times 10^6$ ohms at about 600 seconds whereat the conduit is purged with water, returning the impedance to that of water. At about 1500 seconds, the second solution is introduced to the test apparatus, which causes the impedance to drop to about $8.75 \times 10^5$ ohms at about 1800 seconds, and was then flushed. At about 2600 seconds, the third solution was introduced, which caused the impedance to drop to about $1.00 \times 10^6$ ohms at about 2,900 seconds.

Experiment 4

In a fourth experiment, an interdigitated electrode (IDE), such as a two-electrode gold interdigitated transducer having 10 micrometer (μm) wide electrodes and a spacing between electrodes of 10 μm, was employed. (see FIG. 3) This IDE was coated with an aniline polymer film 12 using an aniline monomer obtained from Aldrich Chemical Co. The aniline monomer was electropolymerized on the surface of the IDE by first subjecting it to a solution of 0.1 M aniline in 1M $H_2SO_4$ and cycling the applied potential between −0.3 volts (V) and 1.1 V versus a silver/silver chloride (Ag/AgCl) reference (50 millivolts per second (mV/sec) scan rate).

The polyaniline (PANI) coated IDE was exposed to samples comprising chloride and sulfate contaminants in ultrapure water. To be more specific, the samples comprised solutions having 40 ppb, 190 ppb, and 151 ppb $ZnCl_2$ and 40 ppb, 190 ppb, and 290 ppb $ZnSO_4$ in water. Information was received from the IDE's via a data acquisition system configured to measure and log the real and imaginary data components of complex impedance in the range of 20 Hz to 1 MHz.

Figure 23:
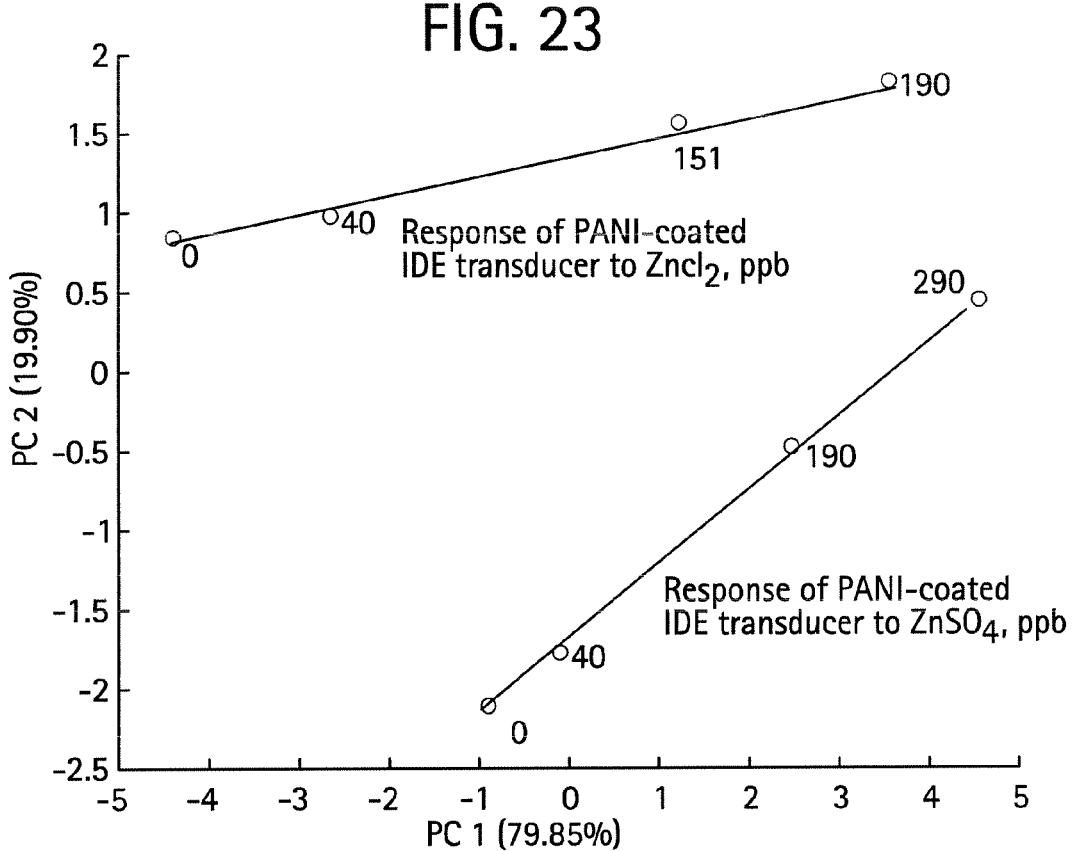
FIG. 23 is an exemplary graphical representation selectivity and sensitivity responses generated during Experiment 4 for a transducer.

Selectivity and sensitivity of the responses provided by the PANI-coated IDE transducer is presented in FIG. 23 as a principal components analysis plot. In the plot, two principal components (PC1 and PC2) are plotted. As can be seen in the plot, the PANI coated IDE exhibits high selectivity and sensitivity in analysis of $ZnCl_2$ and $ZnSO_4$ solutions.

Experiment 5

In this experiment, a method for automatic sensor drift correction is demonstrated. A sulfate sensor film was developed that utilized a formulated polymeric composition such as 31.8 wt % poly(vinylchloride) (PVC), 64.5 wt % plasticizer (such as bis(2-ethylhexyl) sebacate (DOS)), 1.3 wt % neutral salt (tetradodecylammonium tetrakis (4-chlorophenyl) borate (TDDATCPB)), 1.1 wt % ion exchanger (such as tetradodecyl ammonium chloride (TDDMACl)), and 1.3 wt % sulfate ionophore (such as 1,3-[bis(3-phenylthioure-idomethyl)]benzene).

Figure 24:
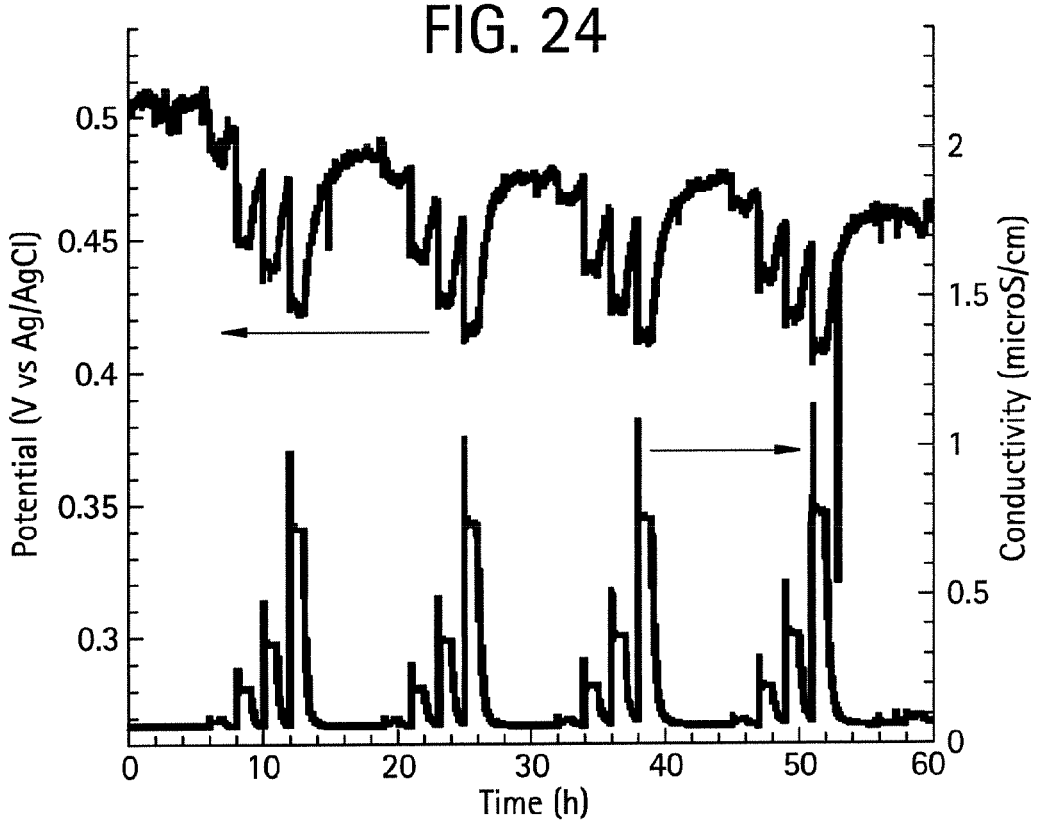
FIG. 24 is an exemplary graphical representation of conductivity and potential for sulfate sensor in Experiment 5.

The sensor film solution was drop coated onto a tip of an electrode, followed by solvent evaporation at room temperature for X hours. Sulfate detection was performed with the resulting sensor by exposing the sensor to 5, 25, 50, and 100 ppb of sulfate ions in ultrapure deionized water. The conductivity of the water was also monitored in parallel with sulfate detection. FIG. 24 shows results of replicate exposures of the sulfate sensor to different sulfate concentrations and simultaneous conductivity measurements, with conductivity provided in microSiemens per centimeter (μS/cm or microS/cm), potential (V vs. Ag/AgCl), and time in hours (h).

FIG. 24 demonstrates a slight but noticeable drift in the sulfate sensor response over 60 hours of testing. Thus, a method has been developed to compensate for this sensor drift. The method utilizes a response of a conductivity probe to correct for the drift in the chemical ions sensor response. The correction is performed by normalizing the response of the chemical ion sensor by the response of the conductivity probe. This correction became possible because of the ultrapure nature of the tested water that mimics the water of nuclear reactors (e.g., the conductivity sensor is sufficiently sensitive to detect a change in conductivity for this particular sample. The conductivity of water of nuclear reactors is typically 0.05 to 0.15 microS/cm and increases in the presence of different ions.) In water with very high background concentration of ions (such as drinking water, tap water, environmental water), such correction using conductivity of water is problematic at best, and essentially impossible. Desirably, the liquid (e.g., water), has a background conductivity (i.e., without the ions of interest), of less than 1 microS/cm.

Figure 25A:
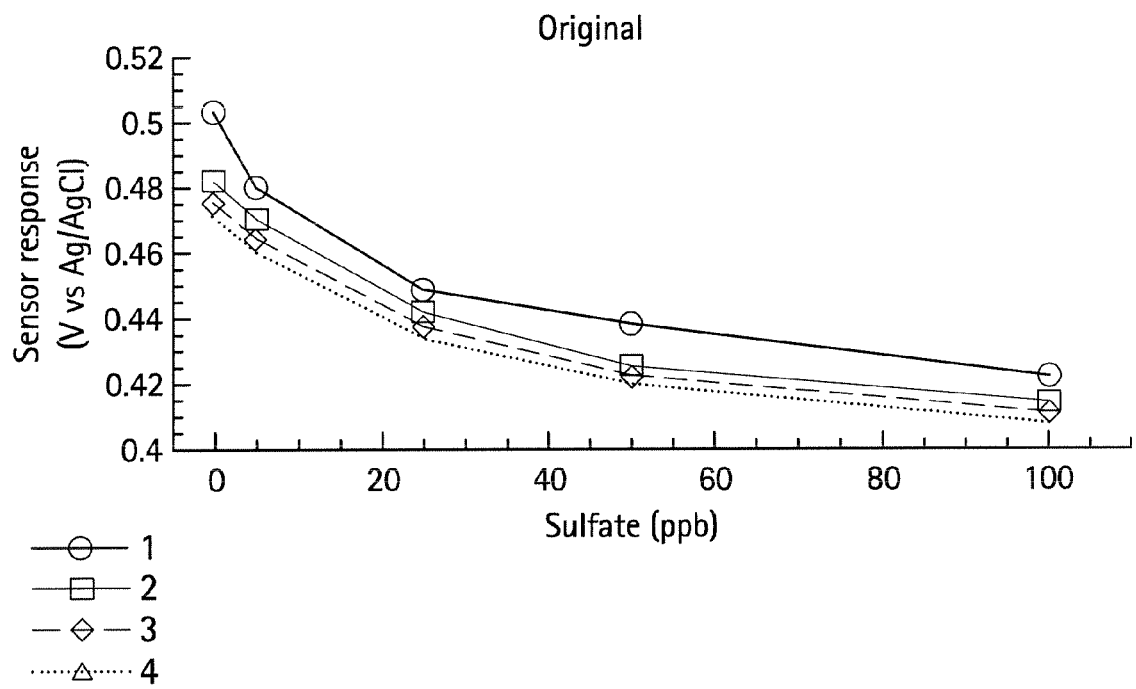
FIG. 25 is an exemplary graphical representation of original and corrected responses for a sulfate sensor generated during Experiment 5.
Figure 25B:
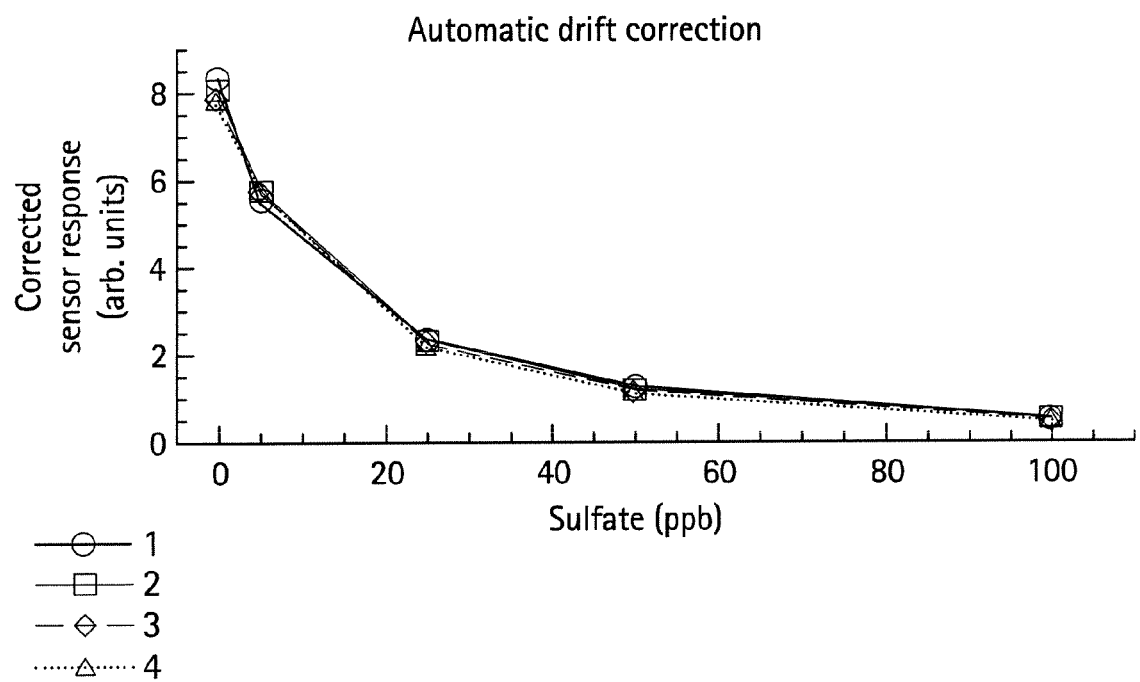

Experimental demonstration of this method is illustrated in FIG. 25. The top graph of FIG. 25 shows an original response of the sulfate sensor upon four replicate exposures to 0, 5, 25, 50, and 100 ppb of sulfate ions (e.g., the results illustrated in FIG. 24 were regraphed in FIG. 25). Clearly, because of the drift in sensor response, these four response curves were offset from each other. Line 1 is for the first set of responses illustrated in FIG. 24 (e.g., up to 15 hours), line 2 is for the second set of responses (e.g., between 15 hours and 30 hours), line 3 is for the third set of responses (e.g., 30 hours to 45 hours), and line 4 is for the fourth set of responses (e.g., 45 hours to 60 hours). However, upon correction (e.g., normalization) of the response of the chemical ion sensor by the change in conductivity value of the liquid (e.g., water), the replicate response curves are more reproducible as shown in the bottom graph of FIG. 25. In other words, using the change in conductivity, compensation for the drift of the sensor was successfully attained.

The disclosed detection methods and contaminant detection systems offer several notable advantages. Firstly, the contaminant detection systems incorporate sensors and sensor arrays that can be purged to remove ions from the sensor's film and transducer that can build up thereon. This ability allows for the calibration of the sensor between sensing modes, which can reduce and/or eliminate interference caused by ion built-up and reduce baseline drift. Further, the sensors and sensor arrays disclosed herein can employ films that selectively allow the transport of ions therethrough. This minimizes interference caused by undesired contaminant ions within the liquid. Yet further, the sensors and sensor arrays can comprise multiple films of differing membranes, which allow the methods for operating the contaminant detection system which enable the system to determine the presence of interfering ions form non-desired contaminants and evaluate the concentration of these interfering ions such that the concentration of these ions can be accounted for to improve the accuracy of the determination of the concentration of the contaminant of interest within the liquid. Yet even further, the sensors and sensor arrays employ a small volume of liquid (e.g., water), which decreases sampling time, and can be configured in a modular design such that components of the sensor can be replaced if needed.

Ranges disclosed herein are inclusive and combinable (e.g., ranges of "up to about 25 wt %, or, more specifically, about 5 wt % to about 20 wt %", is inclusive of the endpoints and all intermediate values of the ranges of "about 5 wt % to about 25 wt %," etc.). "Combination" is inclusive of blends, mixtures, alloys, reaction products, and the like. Furthermore, the terms "first," "second," and the like, herein do not denote any order, quantity, or importance, but rather are used to distinguish one element from another, and the terms "a" and "an" herein do not denote a limitation of quantity, but rather denote the presence of at least one of the referenced item. The modifier "about" used in connection with a quantity is inclusive of the state value and has the meaning dictated by context, (e.g., includes the degree of error associated with measurement of the particular quantity). The suffix "(s)" as used herein is intended to include both the singular and the plural of the term that it modifies, thereby including one or more of that term (e.g., the colorant(s) includes one or more colorants). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments. The terms sensor and probe are used interchangeably herein.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for detecting contaminants in a liquid, comprising:
    contacting a sensor with the liquid, wherein the sensor comprises a film, a purge chamber defined by a manifold having an inlet and an outlet, and a transducer in fluid communication with the purge chamber, and wherein a first surface of the film is in fluid communication with the liquid and the purge chamber is in fluid communication with a second surface of the film that is opposite the first surface, and wherein the film is made of a material that allows ionic transport of the contaminant from the liquid, through the film, and into the purge chamber;
    generating electrical information based upon a concentration of the contaminant in the liquid;
    transmitting the electrical information to a controller;
    determining the concentration of a contaminant in the liquid; and
    purging the purge chamber by causing a purge media to flow through the inlet of the manifold, into the purge chamber such that the purge media is in fluid contact with the transducer, and through the outlet of the manifold.

2. The method of claim 1, further comprising transmitting electrical information from the transducer to the controller in the form of a radiofrequency.

3. The method of claim 2, wherein the electrical information is selected from the group consisting of resonant complex impedance, complex impedance at multiple frequencies, electrochemically-modulated impedance, electrical current, electrical potential, and combinations comprising at least one of the foregoing electrical information.

4. The method of claim 1, further comprising, prior to contacting a sensor with a liquid, thereby preconditioning the liquid.

5. The method of claim 4, wherein the preconditioning further comprises a process selected from the group consisting of temperature adjusting, pressurizing, stirring, mixing with a chemical, and combinations comprising at least one of the foregoing.

6. The method of claim 1, further comprising contacting a conductivity probe with the liquid, determining an electrical conductivity of the liquid, and correcting the concentration of the sample based upon the electrical conductivity.

7. The method of claim 6, comprising using a univariate correction for the correcting the concentration.

8. The method of claim 6, further comprising determining a temperature of the liquid and correcting the electrical conductivity based upon the temperature.

9. The method of claim 1, further comprising contacting a conductivity probe with the liquid in the purge changer, monitoring the conductivity of the liquid, and using a changes in the conductivity as the trigger to process data from the sensor.

10. The method of claim 1, further comprising correcting for bulk effects of the film.

11. The method of claim 10, wherein the bulk effects are selected from the group consisting of leaching of a component of the film, degradation of performance of a component of the film, and combinations comprising at least one of the foregoing.

12. The method of claim 10, wherein the correcting for the bulk effects comprises impedance measurements.

13. The method of claim 10, wherein the correcting for the bulk effects comprises one of potentiometric and impedance measurements.

14. The method of claim 1, further comprising correcting for surface effects of the film.

15. The method of claim 14, wherein the surface effects are selected from the group consisting of surface contamination of the film, erosion of the film, and combinations comprising at least one of the foregoing.

16. The method of claim 14, wherein the correcting for the surface effects of the film comprises impedance measurements.

17. The method of claim 14, wherein the correcting for the surface effects comprises one of potentiometric and impedance measurements.

18. The method of claim 1, wherein the sensor is a potentiometric sensor comprising a working electrode and a reference electrode.

* * * * *